(12) United States Patent
Mark et al.

(10) Patent No.: US 10,806,537 B2
(45) Date of Patent: Oct. 20, 2020

(54) ILLUMINATION SLEEVE

(71) Applicant: Nico Corporation, Indianapolis, IN (US)

(72) Inventors: Joseph L. Mark, Indianapolis, IN (US); Brian C. Dougherty, Indianapolis, IN (US)

(73) Assignee: Nico Corporation, Indianapolis, IN (US)

( * ) Notice: Subject to any disclaimer, the term of this patent is extended or adjusted under 35 U.S.C. 154(b) by 167 days.

(21) Appl. No.: 15/348,575

(22) Filed: Nov. 10, 2016

(65) Prior Publication Data

US 2017/0128150 A1    May 11, 2017

Related U.S. Application Data

(60) Provisional application No. 62/253,957, filed on Nov. 11, 2015.

(51) Int. Cl.
*A61B 90/30* (2016.01)
*A61B 17/32* (2006.01)
(Continued)

(52) U.S. Cl.
CPC .............. *A61B 90/30* (2016.02); *A61B 17/32* (2013.01); *A61B 17/32002* (2013.01); *A61B 90/35* (2016.02); *A61B 17/320758* (2013.01); *A61B 17/320783* (2013.01); *A61B 2017/0046* (2013.01); *A61B 2090/306* (2016.02); *A61B 2090/309* (2016.02)

(58) Field of Classification Search
CPC .......................... A61B 2090/306; A61B 90/35
See application file for complete search history.

(56) References Cited

U.S. PATENT DOCUMENTS

| 1,328,488 | A | * | 1/1920 | Bowden | .................. F16K 27/12 |
| | | | | | 138/89.4 |
| 4,012,155 | A | * | 3/1977 | Morris | .................. F16B 7/0413 |
| | | | | | 403/290 |

(Continued)

FOREIGN PATENT DOCUMENTS

| DE | 4330776 A1 | 3/1995 |
| DE | 102011014772 A1 | 9/2012 |
| DE | 102012110143 A1 | 4/2014 |

OTHER PUBLICATIONS

PCT International Search Report and Written Opinion dated May 12, 2017 for PCT/US2016/061498.

(Continued)

*Primary Examiner* — Jan Christopher L Merene
(74) *Attorney, Agent, or Firm* — Kristin L. Murphy; Honigman LLP

(57) ABSTRACT

A tissue removal system may include a tissue removal device including a handpiece and an upper housing, and configured with an outer cannula having an outer cannula opening for severing tissue, an inner cannula disposed in the outer cannula and reciprocal within the outer cannula, an illumination device having a sleeve arranged at least partially on the outer cannula, and a fiber optic channel defining an opening and arranged offset from the sleeve, and a light source arranged within the channel and configured to supply light from the opening to a surgical site.

16 Claims, 21 Drawing Sheets

(51) Int. Cl.
*A61B 90/35* (2016.01)
*A61B 17/3207* (2006.01)
*A61B 17/00* (2006.01)

(56) References Cited

U.S. PATENT DOCUMENTS

| | | | |
|---|---|---|---|
| 5,569,254 A | 10/1996 | Carlson et al. | |
| 5,873,886 A * | 2/1999 | Larsen | A61B 10/04 606/159 |
| 2003/0095781 A1 * | 5/2003 | Williams | A61B 17/02 385/146 |
| 2006/0173245 A1 | 8/2006 | Todd et al. | |
| 2012/0029354 A1 * | 2/2012 | Mark | A61B 17/32002 600/439 |
| 2012/0033232 A1 * | 2/2012 | Carr | A61B 90/35 356/614 |
| 2012/0078279 A1 * | 3/2012 | Mark | A61B 10/0275 606/171 |
| 2012/0157879 A1 * | 6/2012 | Mark | A61B 10/0275 600/566 |
| 2012/0283718 A1 * | 11/2012 | Cosmescu | A61B 18/1402 606/33 |
| 2012/0289816 A1 | 11/2012 | Mark et al. | |
| 2014/0275806 A1 | 9/2014 | Gunday et al. | |
| 2015/0087998 A1 | 3/2015 | Czupalla et al. | |
| 2015/0297213 A1 * | 10/2015 | Lehtinen | A61B 17/0401 606/232 |
| 2015/0306428 A1 | 10/2015 | Darian | |

OTHER PUBLICATIONS

PCT Partial International Search Report dated Jan. 10, 2017 for PCT/US2016/061498.

* cited by examiner

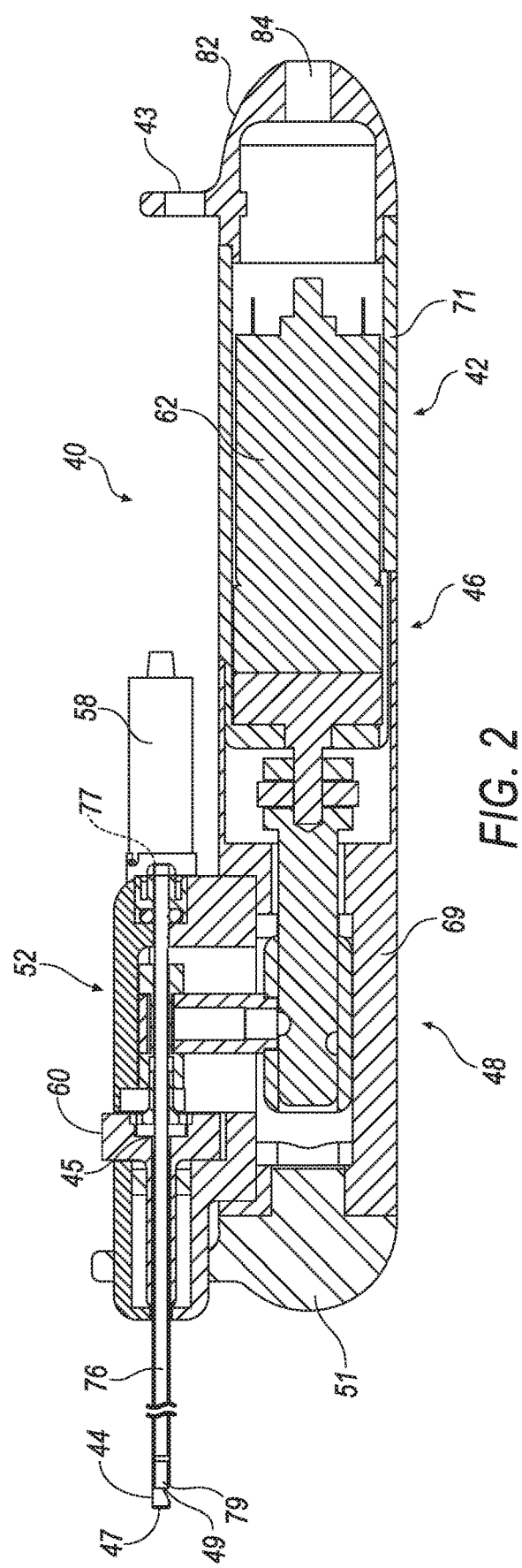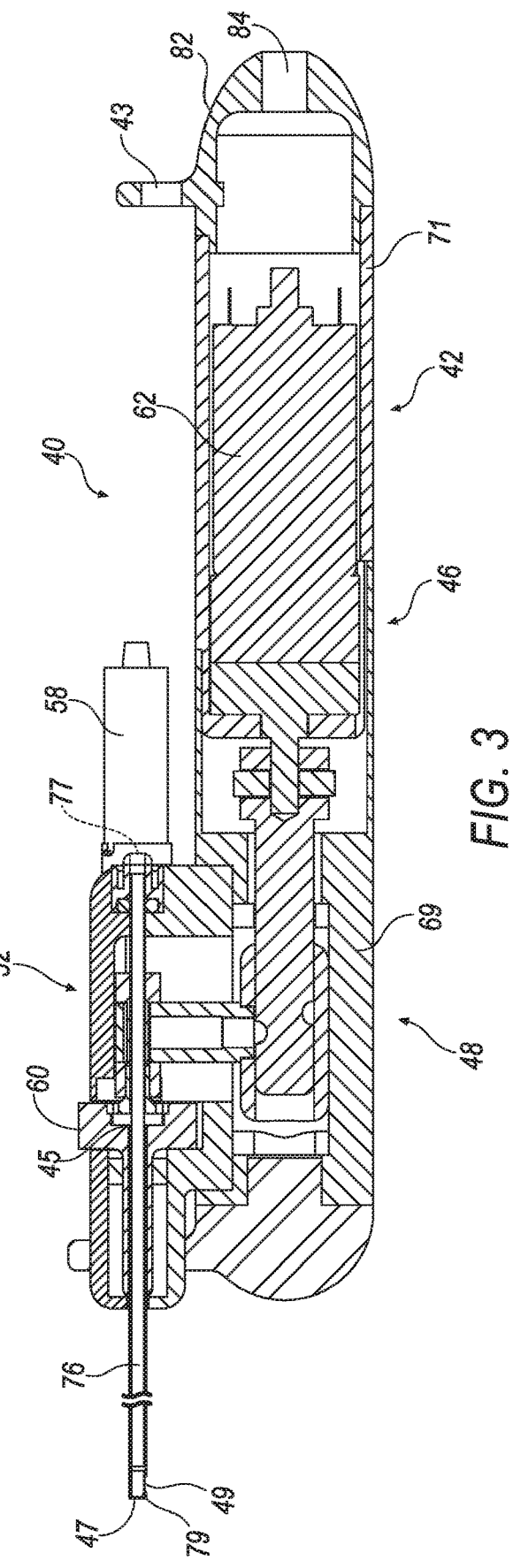

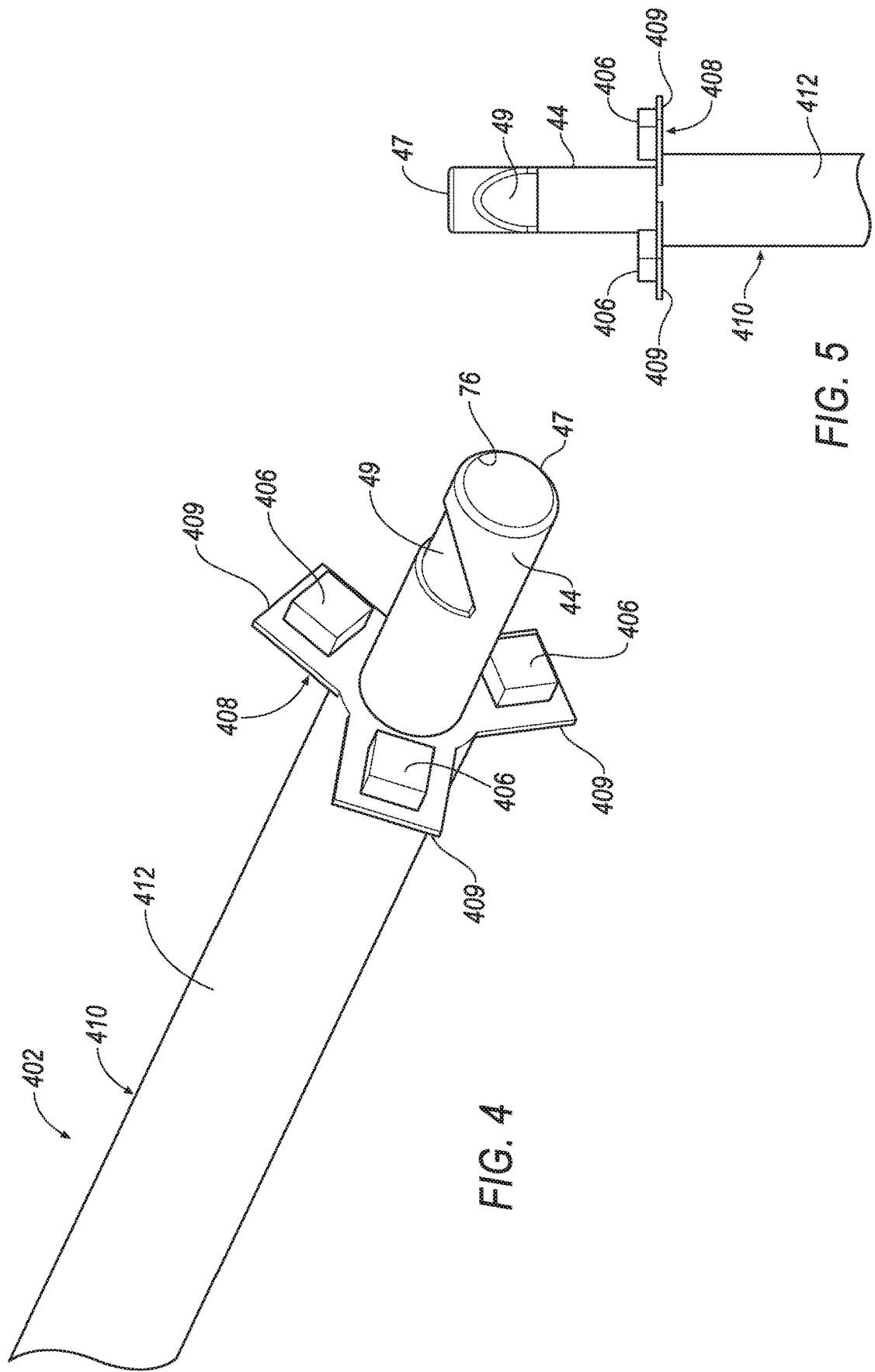

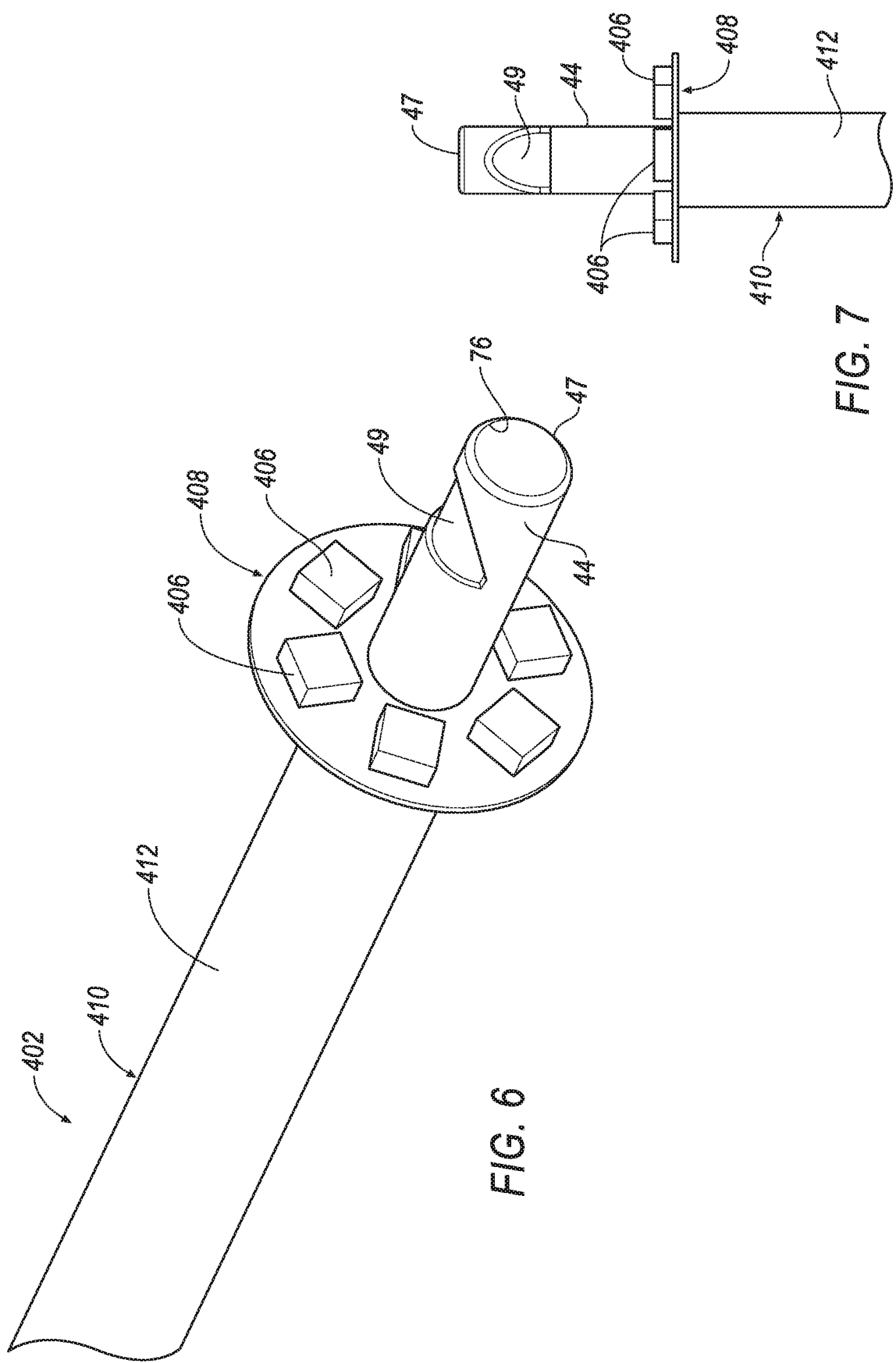

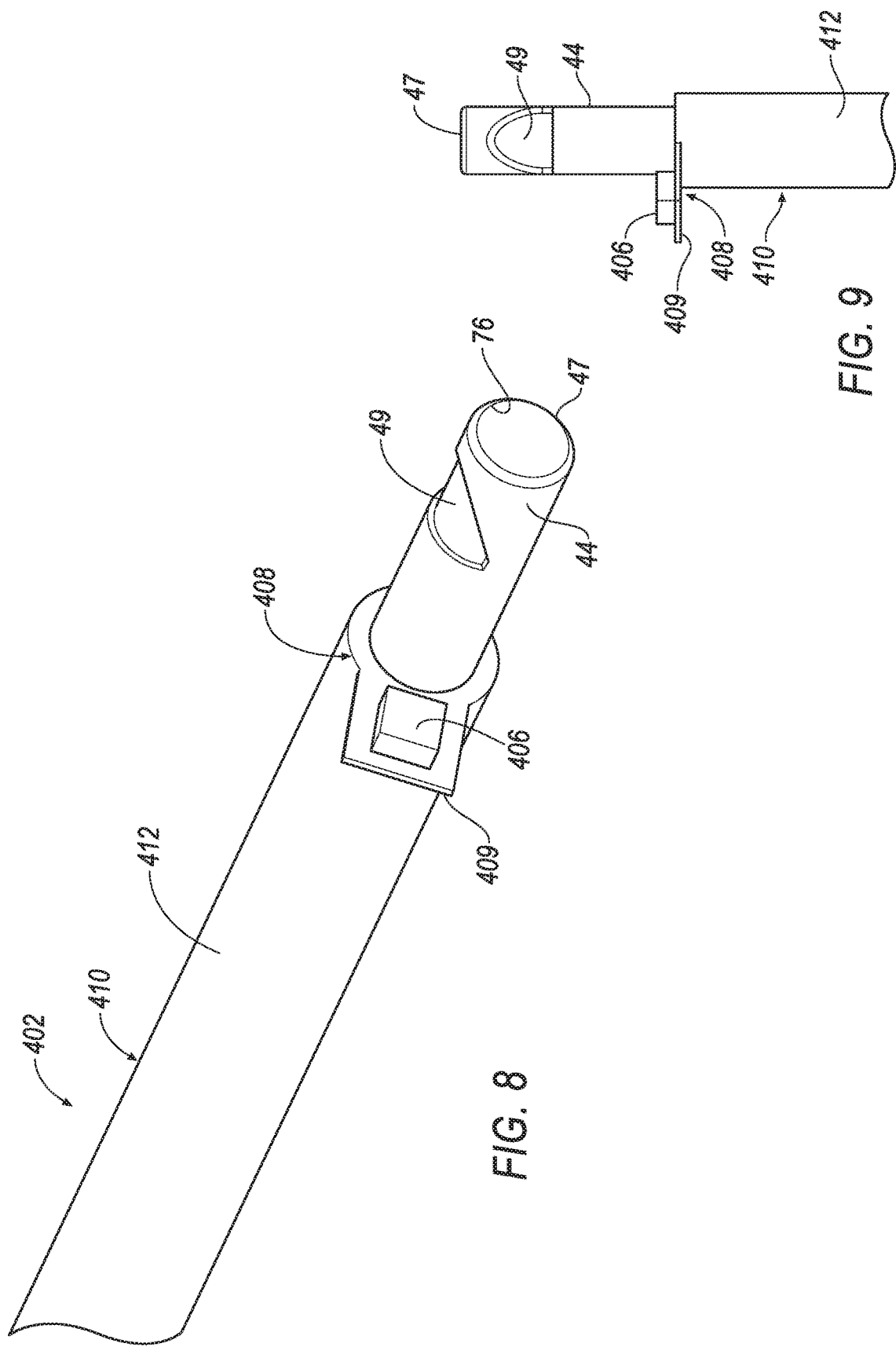

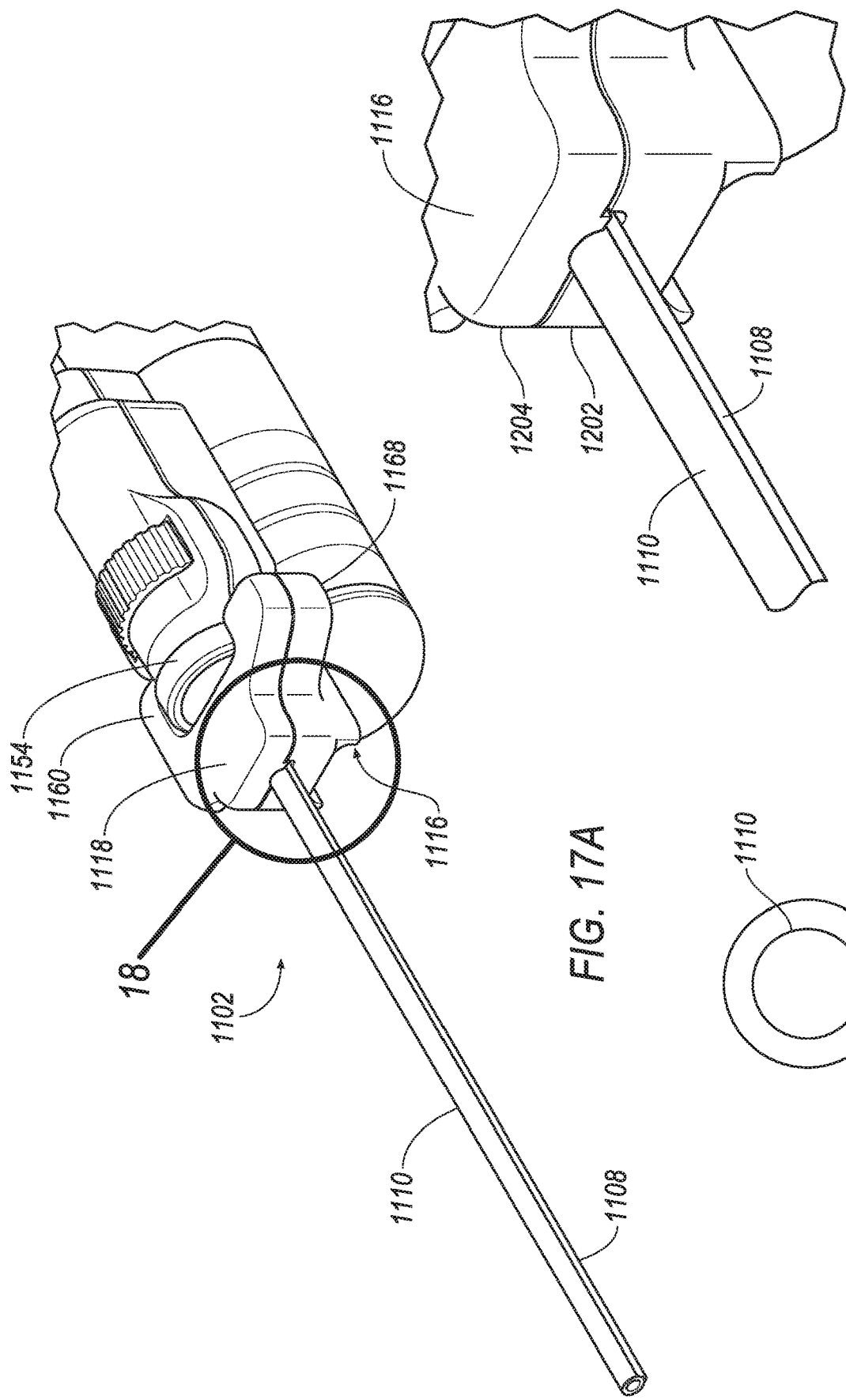

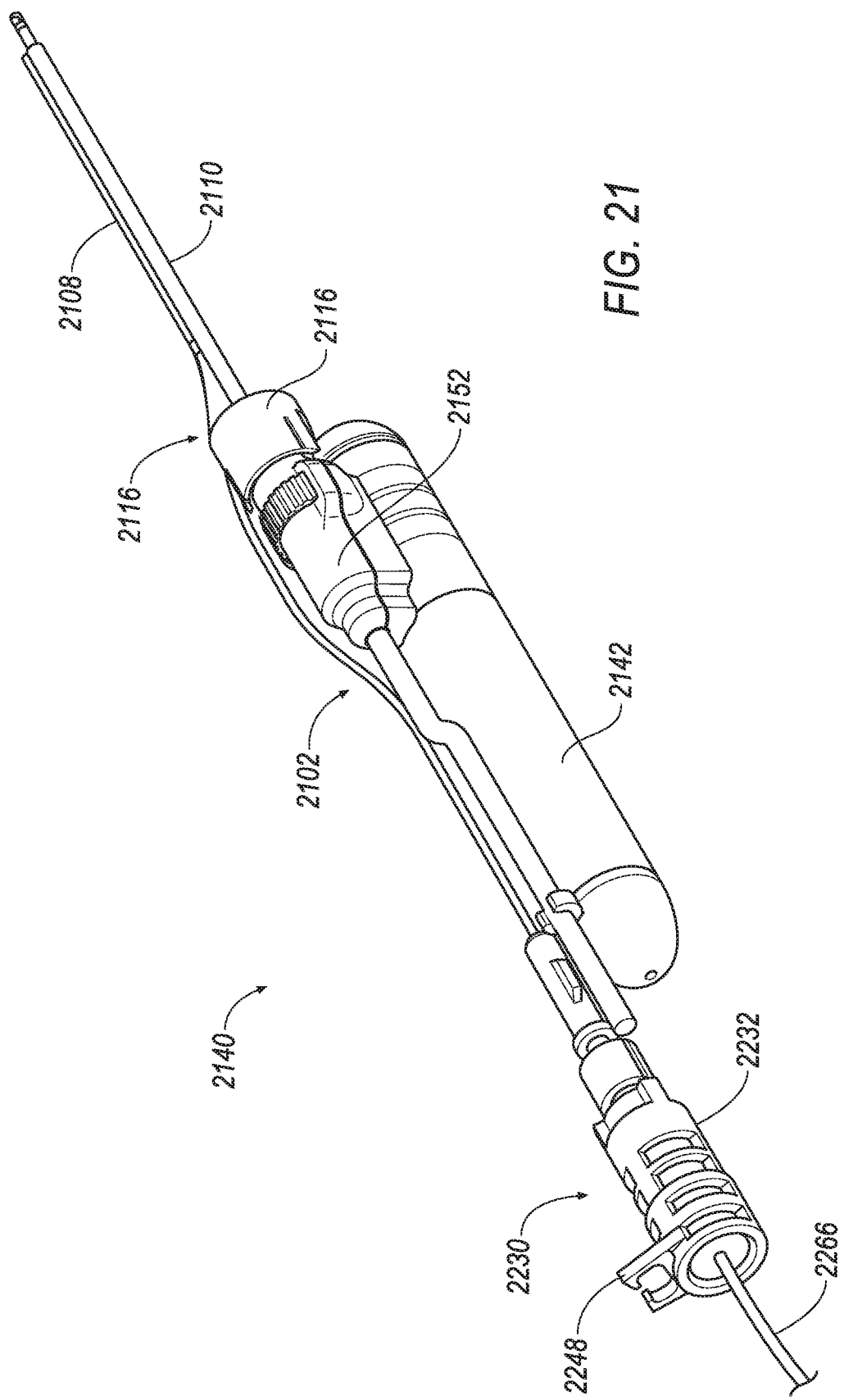

ILLUMINATION SLEEVE

CROSS-REFERENCE TO RELATED APPLICATIONS

This application claims the benefit of U.S. provisional application Ser. No. 62/253,957 filed Nov. 11, 2015, the disclosure of which is hereby incorporated in its entirety by reference herein.

TECHNICAL FIELD

The present disclosure relates to systems and methods for illuminating a surgical site.

BACKGROUND

Various abnormalities of bodily systems, including the neurological system, can cause severe health risks to patients afflicted by them. For example, in connection with a neurological system, abnormalities such as brain and spinal tumors, cysts, lesions, or neural hematomas can lead to deterioration in motor skills, nausea or vomiting, memory or communication problems, behavioral changes, headaches, or seizures. In certain cases, resection of abnormal tissue masses is required. However, given the various complexity and importance of various bodily functions where the abnormality may be found, such procedures may be extremely delicate and must be executed with great precision and care.

Various tissue removal systems are known or have been proposed for excising abnormal tissue from healthy tissue. However, many known tissue cutting devices suffer from an inability to precisely and automatically remove neurological tissue without causing damage to the tissue to be removed, as well as to the surrounding tissues. This disturbance of tissues can take the form of disruption, destruction or even can take the form of "traction" or pull on the surrounding collateral tissue and structures can cause unintended damage to the surrounding tissue. Additionally, various other tissue removal systems use ablative, disruptive or thermal energy, or a combination of these, which may cause damage to the excised tissue, as well as the substrate and collateral tissues. Further, some prior art devices also do not provide for successive excision of tissue samples without removal of each tissue sample between each resection cycle.

Damage to the surrounding tissue can also damage the substrate from which the diseased tissue is excised which is also the "receptor bed" for the delivery and uptake by in-situ tissues for personalized medicine regimens. In addition, many known devices are not configured to both "debulk" large volumes of tissue rapidly near clinically important structures or tissues, as well as be able to finely shave on a cellular layer by layer allowing for control, on or around, more delicate structures, such as vessels, nerves, and healthy tissue. Therefore, the prior art devices lack the flexibility as one instrument, which is required in most neurological procedures. Indeed, many prior art devices simply provide for a ripping or tearing action that removes diseased tissue away from the patient. While some prior art instruments are capable of tissue removal via shaving, these instruments are powered by ablative energy sources. Accordingly, these tissue removal mechanisms are not suitable for use when the integrity and viability of the tissue is desired to be maintained for subsequent use for the formulation of personalized medicine regimens. Nor do they allow for the capture and preservation of the resected tissue within a sterile environment. Additionally, the ablative energy that these devices generate also affects the collateral tissue, such as the substrate from which the tumor has been resected which causes the substrate to be damaged and less or even non-effective as a "receptor bed" for subsequent in-situ personalized medicine regimens.

Currently evolving treatment protocols for certain diseases call for patient specific targeted therapies, i.e., personalized medicine. Several forms of personalized medicine utilize diseased tissue from the patient, i.e., excised tissue, to obtain information about the general disease type, as well as the specific genetic and molecular make-up of the patient's specific disease. From this information, a targeted or personalized oncological treatment regimen may be developed that requires the use of the patient's own tissue, which is cultured and used to create a patient specific "cocktail" which may then be delivered back into the patient as a tailored specific therapy regime for that patient.

The current challenge for prior art tissue cutting devices is the ability to achieve a safe and effective Gross Total Resection (GTR) or near GTR, to provide the lab with intact segments (biopsy quality tissue, not just cells or macerated tissue) of patient's tissue with little to no crush artifact. Consistency in the "bite" size of the resected tissue is also a challenge. Same or near same sized dimensionally resected tissue bites would minimize post processing handling for oncological use and culturing. A slurry of cells or macerated tissue is not very useful for pathology and unacceptable for an effective oncologically based treatment protocol when tissue culturing is required. Current resection techniques and devices do not effectively deliver what is required.

The tissue resected by the surgeon, analyzed by the pathologist and used by oncology is the source of crucial information, and that same tissue is used to create, from the patient's own tissues, the appropriately effective treatment protocol to be used. Indeed, the surgically resected tissue possesses the generic, proteomic and molecular information needed to define the specific characteristics of the patient's tumor, the specific therapies to which the tumor would be expected to respond, and even the specific risks of adverse reactions to given therapies predicted by the patient's tumor make-up.

Thus, a need has arisen for a system that utilizes a tissue cutting device that addresses the foregoing issues, as well as a system that provides for effective transport of resected tissue while minimizing degradation, if not eliminating detrimental stress on the tissue samples.

SUMMARY

A tissue removal system may include a tissue removal device including a handpiece and an upper housing, and configured with an outer cannula having an outer cannula opening for severing tissue, an inner cannula disposed in the outer cannula and reciprocal within the outer cannula, an illumination device having a sleeve arranged at least partially on the outer cannula, and a fiber optic channel defining an opening and arranged offset from the sleeve, and a light source arranged within the channel and configured to supply light from the opening to a surgical site.

An illumination device for tissue removal system may include a sleeve arranged at least partially on an outer cannula of a tissue removal system, the sleeve including a light source to provide light to a surgical site at a distal sleeve opening, and to selectively attach to the tissue removal system and maintain the sleeve therein.

An optic attachment assembly for tissue removal system may include a sleeve arranged at least partially on an outer cannula of a tissue removal system, the sleeve including a fiber optic cable, and a housing including a light source configured to provide light to the fiber optic cable, the housing including a cage surrounding the light source to prevent exposure to the light source.

BRIEF DESCRIPTION OF THE DRAWINGS

Embodiments of the present disclosure will now be described by way of example in greater detail with reference to the attached figures, in which:

FIG. 2 is a cross-sectional view of the tissue cutting device of FIG. 1 depicting an inner cannula in a first relative position with respect to an outer cannula in which the inner cannula's distal end is located proximally of the outer cannula's distal end;

FIG. 3 is a cross-sectional view of the tissue cutting device of FIG. 1 depicting the inner cannula in a second relative position with respect to the outer cannula in which the inner cannula's distal end is located at the distal end of the outer cannula;

FIG. 4 is a perspective view of a portion of an illumination device of FIG. 1;

FIG. 5 is a top view of a portion of the illumination device of FIG. 4;

FIG. 6 is a perspective view of a portion of another illumination device;

FIG. 7 is a top view of a portion of the illumination device of FIG. 4;

FIG. 8 is a perspective view of a portion of another illumination device;

FIG. 9 is a top view of a portion of the illumination device of FIG. 4;

FIG. 17A is another perspective view of a portion of the illumination device of FIG. 11

FIG. 17B is a cross-sectional view of the sleeve and the channel of FIG. 17B;

FIG. 18 is another perspective view of a portion of the illumination device of FIG. 11;

FIG. 21 is a perspective view of a tissue cutting device including an illumination device in accordance with a another embodiment;

DETAILED DESCRIPTION

Figure 1:
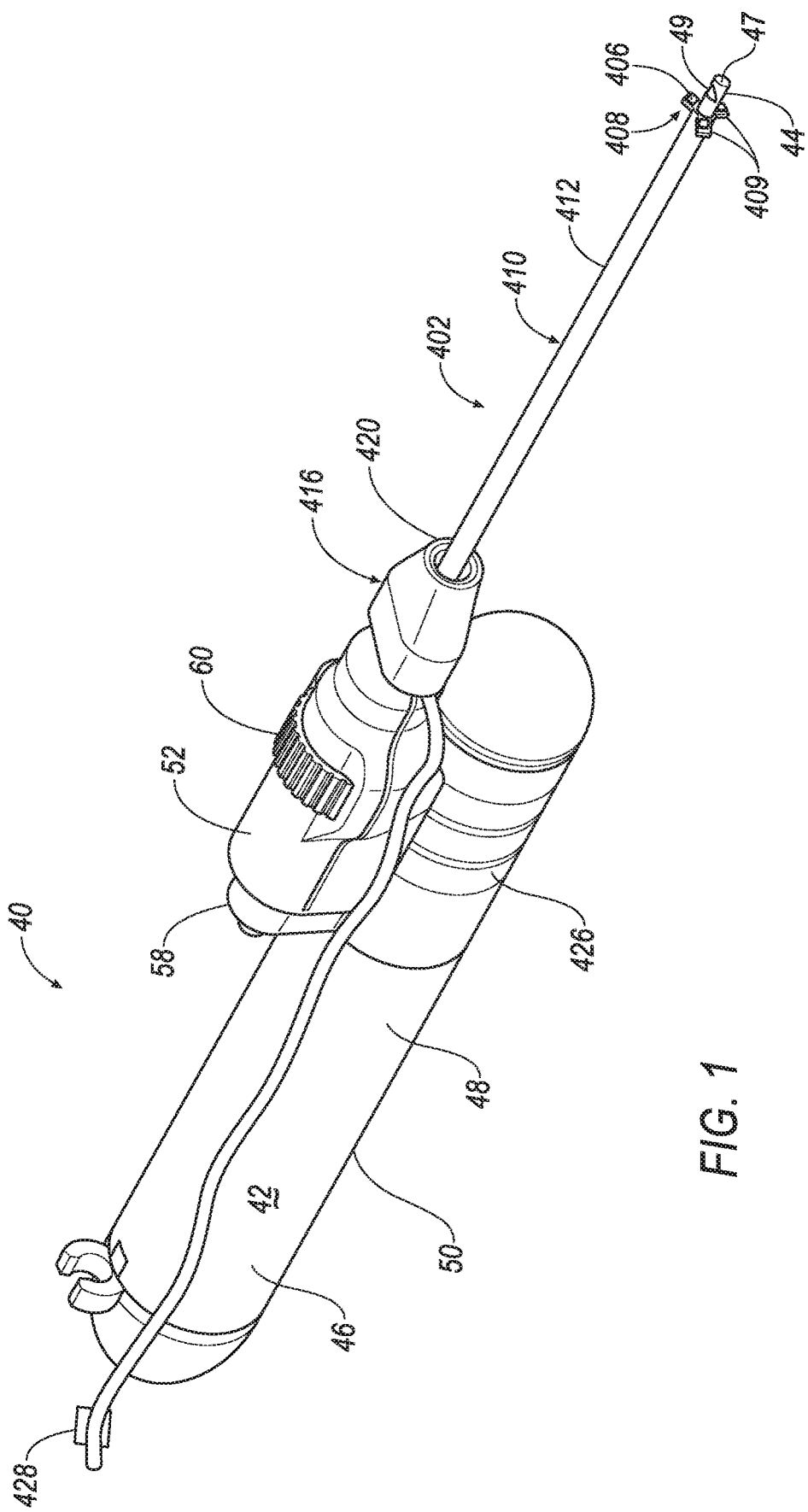
FIG. 1 is a perspective view of a tissue cutting device including an illumination device in accordance with a first embodiment.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein are tissue cutting devices that are suited for surgical applications. While described herein in connection with neurosurgical applications such as the removal of spine and brain tissue, it is understood that the disclosure herein is applicable to other surgical applications and treatment protocols. As described herein, the devices may be configured with an illumination device configured to supply light to a surgical site, reduce the shadowing effects typically created by non-local light sources, and provide specific wavelengths of light to specific regions of a surgical site. The illumination device may include a sleeve arranged around the outer cannula and an attachment hub to be arranged at the proximal end of the outer cannula. One or more light sources, such as light emitting diodes (LEDs) may be arranged at the distal end of the sleeve for providing light to the surgical site. The light sources may also be in the form of a fiber optic-cable exposed at the distal end of the sleeve.

Referring to FIG. 1, a tissue cutting device 40 includes a handpiece 42 and an outer cannula 44. In one exemplary embodiment, handpiece 42 is generally cylindrical in shape and is preferably sized and shaped to be grasped with a single hand. Handpiece 42 includes a lower housing 50 which comprises a proximal section 46 and distal section 48. Lower housing 50 comprises a proximal-most housing portion 82 (FIGS. 2 and 3) that is connected to a motor housing 71, and a cam housing 69 that is connected to motor housing 71. A front housing section 51 is connected to cam housing 69. Upper housing 52 is also provided that supports the outer cannula. A tissue collector 58 may be operatively connected to upper housing 52, either directly or remotely via appropriate tubing. A rotation dial 60 for rotating the outer cannula 44 (FIGS. 2 and 3) with respect to handpiece 42 is also mounted to upper housing 52.

As best seen in FIGS. 2 and 3, outer cannula 44 includes an open proximal end 45, a closed distal end 47, and a distal opening 49 proximate distal end 47. Tissue cutting device 40 further comprises an inner cannula 76 which is partially disposed in an outer cannula lumen (not shown). Inner cannula 76 is configured to reciprocate within outer cannula lumen and to cut tissue samples entering outer cannula 44 via outer cannula distal opening 49, without crush artifact or thermal damage. Inner cannula 76 reciprocates between a proximal position, which is depicted in FIG. 2 and a distal position which is depicted in FIG. 3. Inner cannula 76 includes an open proximal end 77 and an open distal end 79. Distal end 79 is configured to cut tissue, and in exemplary embodiments, is capable of cutting neurological system tissues such as those from the brain or spine. In one exemplary embodiment, inner cannula distal end 79 is beveled in a radially inward direction to create a sharp circular tip and facilitate tissue cutting. Outer cannula 44 may not be translatable with respect to handpiece 42 such that its position with respect to handpiece 42 along the direction of the longitudinal axis of handpiece 42 remains fixed.

An example illumination device 402 is shown in FIG. 1 and may be selectively attachable to the handpiece 42. The illumination device 402 may be arranged around the outer cannula 44 and configured to supply light to a surgical site via one or more light sources 406 arranged on a lip or distal aspect 408 of a sleeve 410. The distal aspect 408 may extend radially outwardly from a distal end of the sleeve 410. The distal aspect 408 may form one or more projections configured to maintain the light source 406. The distal aspect 408 may also form a solid lip, as depicted and described below with respect to FIGS. 6 and 7. The light sources 406 may be arranged on the underside of the distal aspect 408 so as to face and emit light toward or at the distal end 47 of the outer cannula 44.

The sleeve 410 may form a tube-like channel configured to surround the outer cannula 44. The sleeve 410 may include or be comprised of a flexible circuit board configured to provide power to the light source 406. The sleeve 410 may have an elongated channel section 412 connected to an attachment hub 416, whereby the channel section 412 extends distally away therefrom. The illumination device 402 is shown in an installed condition in FIG. 1 wherein the illumination device 402 may be selectively positionable along the length of the outer cannula 44. During installation, the attachment hub 416 and the channel section 412 may be slid onto the outer cannula 44 at the distal end 47 of the outer cannula. The attachment hub 416 may include a friction element that can grip the outer cannula 44 to position the illumination device 402 at a variety of locations along the outer cannula 44.

The sleeve 410 may be rigid or semi-rigid and made of a material that is suitable for use with sterilization techniques, such as ethylene oxide sterilization, Sterrad, autoclaving and gamma radiation sterilization. The sleeve may include resins and metals, and may be formed of material similar to a printed circuit board (PCB). The sleeve 410 may be a flexible PCB such that during manufacturing the board may be curved to form the tube-like shape. Further, the sleeve 410 may be made of several materials in addition to, or as an alternative to the PCB. In one example, the PCB may be surrounded by or overlaid with a polymer material, polyimide, polyamides, etc. The flexible sleeve 410 is discussed in more detail herein with respect to FIG. 7 and FIG. 10 below.

Referring to FIG. 1, the attachment hub 416 may include an interior channel (not shown) for receiving the outer cannula 44 during installation. The attachment hub 416 may also include a sleeve channel 420 configured to receive at least a portion of the sleeve 410. The sleeve 410 and the attachment hub 416 may be connected in any number of ways, including with adhesives, mechanical fasteners, as well as other mechanisms such as welding and soldering. In addition, the sleeve 410 may be integrally formed with the hub 416 such as by integrally molding the channel section 412 and hub 416 as a single piece.

The attachment hub 416 may be connected to a cord 426 configured to provide electric power to the attachment hub 416 and subsequently the sleeve 410. The cord 426 may be connected directly to the sleeve 410 within the hub 416 whereby the cord 426 may supply power directly to the sleeve 410. In this example, the hub 416 may provide a structure to maintain and protect the connection between the cord 426 and the sleeve 410. In another example, the hub 416 may provide an electrical connection with the cord 426 and another electrical connection with the sleeve 410 so that power is transmitted through the connections. The hub 416 may provide a cord opening (not labeled in FIG. 1) whereby the hub 416 receives the cord 426.

The attachment hub 416 may be configured to be applied to and removed from the outer cannula 44. The hub 416 may provide for various forms of fixation to the outer cannula 44. For example, the hub 416 may clamp onto or provide a friction fit to the cannula 44 or the hub 1116, as discussed below with respect to FIG. 12. In other examples, the hub 416 may fasten to the outer cannula 44 by a mechanical attachment such as a clamp, lock and pin, etc. In other examples, the attachment hub 416 may attach to the upper housing 52.

The attachment hub 416 may also include exterior surface features which enhance the user's ability to grip the hub 416 such as when the sleeve 410 is being slid along outer cannula 44 to position the sleeve 410 along the length of outer cannula 44. In one example, a plurality of longitudinally oriented grooves are spaced apart from one another around the circumference of hub 416 (not shown) and are provided to facilitate gripping. In another example, a plurality of protruding axially oriented ridges (not shown) are provided and are spaced apart around the circumference of the hub 416.

The cord 426 may be maintained along the handpiece 42 with various clips or connectors (not shown in FIG. 1). A switch 428 may be arranged on the cord 426 to open and close a connection with a power source (not shown), thereby selectively providing power to the sleeve 410 via the cord 426. By opening and closing power to the sleeve 410, power is also opened and closed with respect to the light sources 406. In another example, power may be supplied directly from the handpiece 42 or from a console that provides power to the handpiece 42.

In one example, when the sleeve 410 is in an installed condition on outer cannula 44, outer cannula 44 may be rotated with respect to the sleeve 410. In one illustrative example, the surgeon may grip hub 416 with the fingers of one hand to restrain its rotational movement and rotate outer cannula rotation dial 60 with the thumb and/or fingers of the other hand to adjust the circumferential position of outer cannula opening 49. While the sleeve 410 may be configured to rotate with outer cannula 44, in many instances it is preferable to maintain the circumferential orientation of sleeve 410 in order to prevent cord 426 from twisting.

In FIGS. 2-3, sleeve 410 is not shown for ease of viewing. Motor 62 is disposed in proximal lower housing section 46 of handpiece 42 and is operably connected to inner cannula 76 to drive the reciprocation of inner cannula 76 within outer cannula lumen. Motor 62 may be a reciprocating or rotary motor. In addition, it may be electric or hydraulic. However, in the embodiment of FIGS. 2 and 3, motor 62 is a rotary motor, the rotation of which causes inner cannula 76 to reciprocate within outer cannula lumen.

Motor 62 is housed in motor housing 71, which defines a portion of proximal lower housing section 46. Motor 62 is connected to an inner cannula drive assembly which is used to convert the rotational motion of motor 62 into the translational motion of inner cannula 76. At its proximal end, motor housing 71 is connected to proximal-most housing portion 82, which includes a power cable port 84 and a hose connector 43, which in the exemplary embodiment of FIG. 3 is configured as an eyelet. However, it is understood that hose connector 43 may embody other configurations. Hose connector 43 provides a mechanism for securely retaining a vacuum system hose to handpiece 42, thereby allowing vacuum to be supplied to tissue collector 58. Additionally or alternatively, the cord 426 may also be secured within the hose connector 43.

FIG. 4 illustrates a detailed view of the illumination device 402 of FIG. 1. As explained, the illumination device 402 includes the sleeve 410 having the channel section 412 extending between a proximal end and the distal aspect 408. The distal aspect 408 includes a plurality of projections 409, each configured to retain one of the light sources 406. The distal aspect 408 may be arranged proximate to the distal end 47 of the outer cannula 44, whereby the outer cannula opening 49 may be accessible to cut tissue samples. The light sources 406 may provide light to the surgical site. The light sources 406 may be light emitting diodes (LEDs) or other low-energy consuming light sources 406. The LEDs may provide targeted illumination to a specific surgical site without otherwise causing a distraction or affecting other external room lighting. The example in FIG. 4 illustrates the distal aspect 408 having three (3) projections 409 with a light source 406 arranged at each projection 409. However, any number of projections 409 and light sources 406 may be implemented.

FIG. 5 illustrates a top view of the illumination device 402 of FIG. 4. While the projections 409 are illustrated as being oriented at an approximate 90° angle with respect to an axis extending through the sleeve 410, it is understood that the projections may be oriented at other angles. For example, in the embodiment the projections 409 may be angled toward the axis extending through the sleeve to focus the light from the LEDs.

FIG. 6 illustrates another example illumination device 402. In the example of FIG. 6, the distal aspect 408 forms a solid circular lip configured to retain a plurality of light sources 406. Although FIG. 6 illustrates six (6) light sources 406, this is merely exemplary, and more or less may be included.

FIG. 7 illustrates a top view of the illumination device 402 of FIG. 6.

FIG. 8 illustrates another example illumination device 402 where the distal aspect 408 includes a single projection configured to retain a single light source 406. While a single light source 406 is shown, more than one light source 406 may be included on a single projection 409.

FIG. 9 illustrates a top view of the illumination device 402 of FIG. 8.

Figure 10:
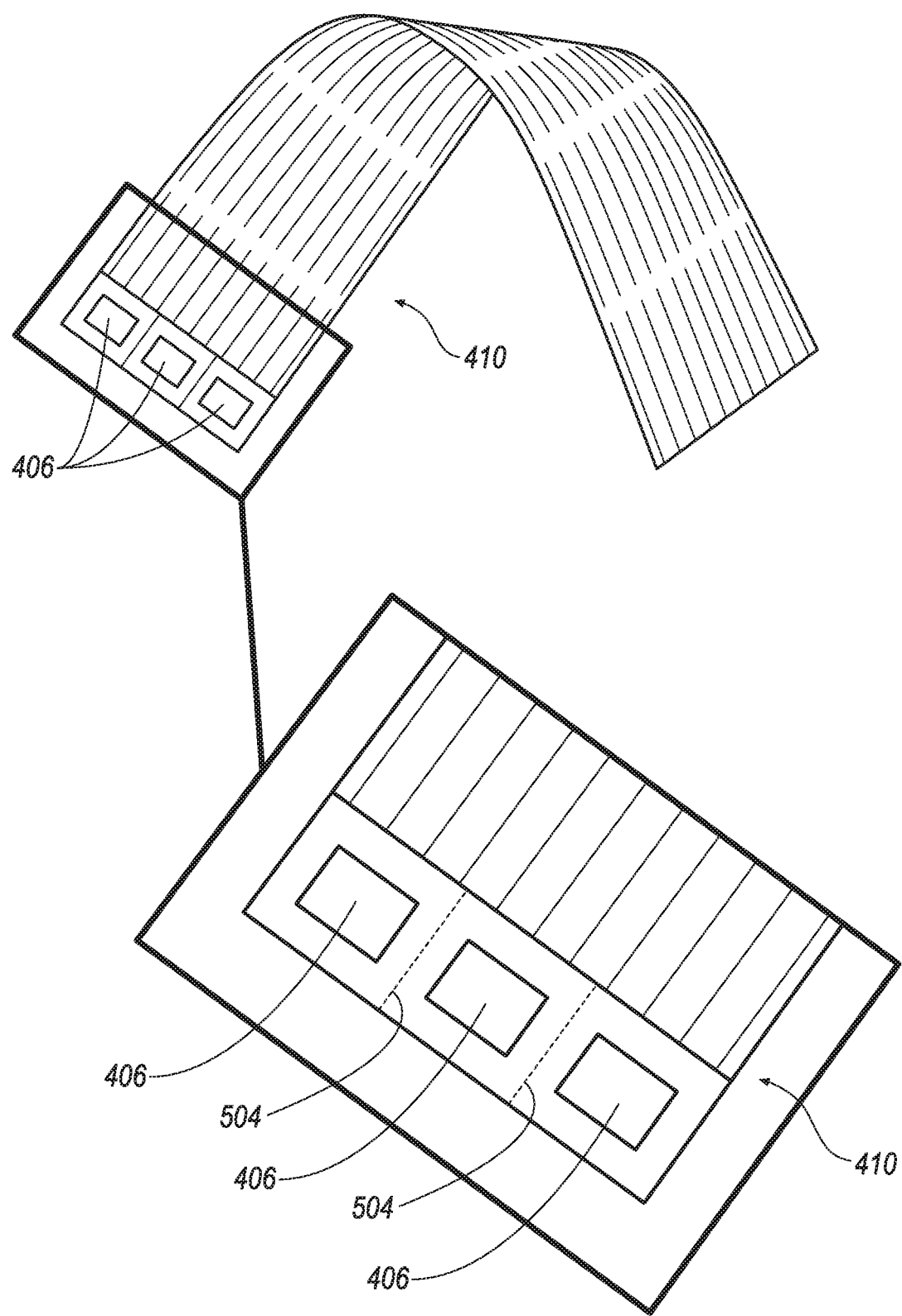
FIG. 10 is a perspective view of a portion of a sleeve of the illumination device of FIGS. 1 and 6

FIG. 10 illustrates an example sleeve 410 in an uninstalled state whereby the sleeve 410 is formed out of a PCB. The PCB may include various electrically conductive tracks in order to supply power from the power source (not shown) to the light sources 406. During manufacturing of the sleeve 410, the light sources 406 may be adhered to the underside of the PCB (e.g., soldered). The PCB may be perforated along perforation lines 504 between the light sources 406. The PCB may then be rolled into a tube-like shape, opposite ends thereof being connected or adhered to one another via a connecting mechanism (e.g., soldering, welding, gluing, external clamps, etc.). As the PCB is rolled, the portions hosting the light sources 406 may begin to separate from one another at the perforated lines 504, thus forming the distal aspect 408, as shown in FIGS. 1 and 4. The projections may then be bent outwards so as to be perpendicular, nearly perpendicular, or other desired angle, to the formed channel section 412. The light source 406 at the underside of the distal aspect housing may then face outward at the distal end of the sleeve 410. The sleeve 410 may be formed of a single PCB piece thus allowing for a simple manufacturing process.

As explained, the light sources 406 may be powered via a power source (e.g., a wall-outlet power source or external battery power source or the handpiece or the handpiece console.) The cord 426 may deliver power to the hub 416, which in turn may deliver power to the sleeve 410. The light sources 406, in one example, may include white light sources. In other examples, the lights sources 406 may be configured to emit one or more in combination of different light frequencies. In use, various dyes (e.g., 5-aminolevulinic acid hydrochloride such as Gliolan™) may be applied to the tissue. Depending on the type of fluorescing characteristics induced such as by an exogenously source (a dye or similar) or endogenously occurring within the tissue the wavelength of the light may be changed. The type of light frequency desired may depend on the type of dye being used so as to create an appropriate reaction with the dye.

The light frequency may be selected at the switch 428. In one example, the switch may include a dial configured to adjust the light intensity where the dial may adjust the amount of power supplied to the sleeve 410 and subsequently the light source 406. This may be achieved using an alternating switch or variable resistor. Additionally or alternatively, the switch 428 may include a multi-position switch such as a rotary switch or rocker switch in order to control the power. The voltage may be configured to control the intensity of the light, as well as frequency-specific diodes within the LEDs in order to alter the light frequency.

Figure 11:
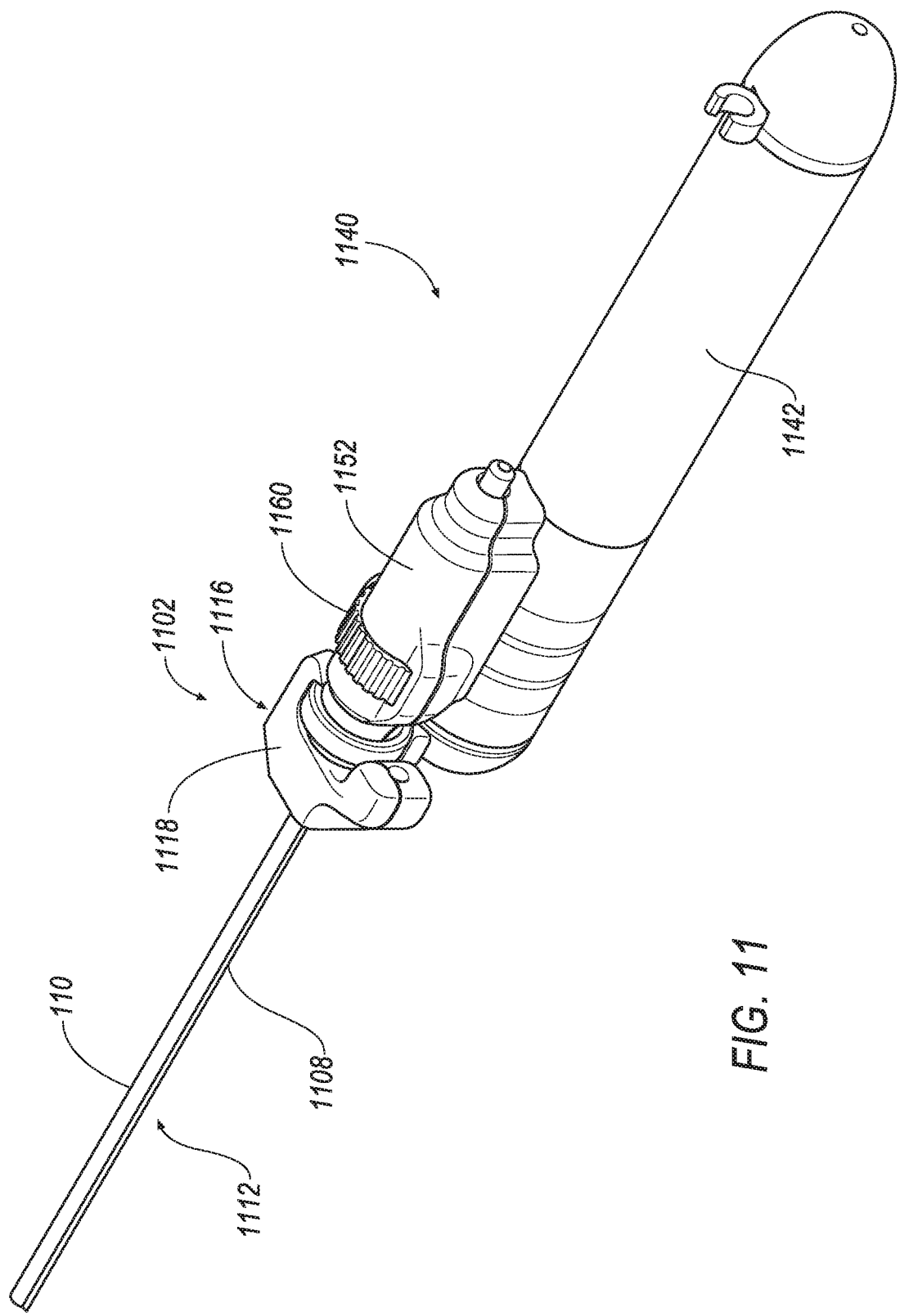
FIG. 11 is a perspective view of a tissue cutting device including an illumination device in accordance with a first embodiment.

FIG. 11 illustrates another example tissue cutting device 1140 that includes a handpiece 1142. FIG. 11 also illustrates another example illumination device 1102 that may be selectively attachable to the handpiece 1142. The illumination device 1102 may be arranged around the outer cannula 44 (not visible in FIG. 11) and configured to supply light to a surgical site via one or more fiber optic devices 1112 arranged on a sleeve 1110. The sleeve 1110 may form a tube-like channel configured to surround the outer cannula 44. The fiber optic device 1112 may include a fiber optic channel 1108 configured to retain at least one fiber optic cable (not shown) configured to supply light to the surgical site at the distal end of the outer cannula 44. The fiber optic cable may extend from within the hub 1116 through the end of the channel 1108, delivering light to the surgical site. The sleeve 1110 and the channel 1108 may be connected via molding, soldering, heat shrinking, etc. In one example, the fiber optic channel 1108 may be the fiber optic cable. That is, a separate channel may not be necessary and instead the fiber optic cable may be directly be adhered to the sleeve 1110.

Figure 12:
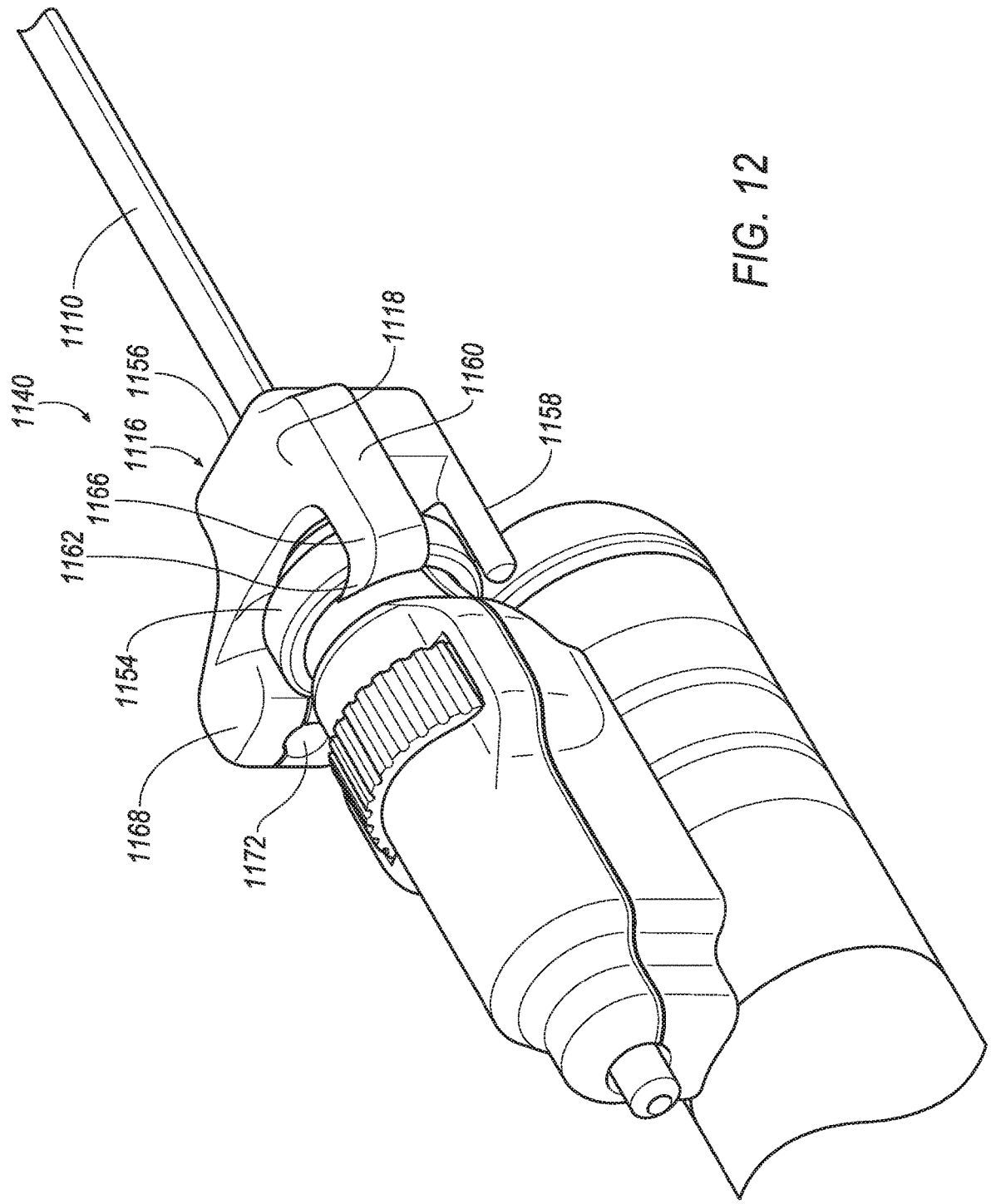
FIG. 12 is another perspective view of a portion of the illumination device of FIG. 11.

An attachment hub 1116 may be configured to attach and detach from the outer cannula 44 at the upper housing 1152 of the handpiece 1142. The attachment hub 1116 may be configured to "snap" on to a portion of the upper housing 1152. As best seen in FIG. 12, the attachment hub 1116 may include a hub body 1118 configured to selectively attach to the upper housing 1152. In the examples discussed herein, the hub body 1118 may be configured to connect to the upper housing 1152 via a snap-fit about a rim 1154 at the distal end of the upper housing 1152. The hub body 1118 may include at least one projection extending from a distal end 1156 of the hub 1116 to a projection distal end 1162. As shown in the examples herein, the at least one projection may include a first projection 1158 and a second projection 1160.

The first projection 1158 may include a rod-like shape or cylinder-like shape, as shown in FIG. 12. The second projection 1160 may include a cuboid-like shape and may include a tapered end 1166. The tapered end 1166 may include a concave-like shape configured to form a lip 1162. In an installed state, the tapered end 1166 may be configured to engage the rim 1154 to secure the attachment hub 1116 to the upper body 1152 via the lip 1162.

The attachment hub 1116 may be made of a rigid or semi rigid material such as plastics, metals, etc., or any combination thereof. The attachment hub 1116 may be formed via injection molding and may be formed as a single piece. Additionally or alternatively, the attachment hub 1116 may include a first portion 1202 and a second portion 1204, as described in more detail below with respect to FIGS. 17 and 19.

While the hub body 1118 may be relatively rigid in order to maintain the sleeve 1110 there within, the projections 1158, 1160 may be flexible so as to deflect outwardly while being slid over the rim 1154, and to retract and engage an underside of the rim 1154 in the installed state/condition. That is, the tapered end 1166 may expand outwardly over the rim 1154 and then retract inwardly once the rim 1154 has been cleared so that the lip 1162 may engage the underside of the rim 1154 to secure the attachment hub 1116 to the upper body 1152.

The attachment hub 1116 may be configured to receive the sleeve 1110 and the fiber optic channel 1108, each of which may be soldered, or molded to within their respective channels in the attachment hub 1116, as discussed below.

The attachment hub 1116 may also include a wire housing portion 1168 arranged across and opposite of the first and second projections 1158, 1160. The wire housing portion 1168, which is described in more detail with respect to FIG. 13 below, may define a channel opening 1172. As shown in FIG. 12, the attachment hub maintains the sleeve 1110 on the upper portion 1152. The wire housing portion 1168 may abut at least a portion of the upper housing 1152, including at least a portion of the rim 1154. At least the second projection 1160 may engage the opposite side of the rim 1154 thus creating an opposing force on the rim 1154. The wire housing portion 1168 and the projections 1158, 1160 may therefore impart forces against the rim 1154, creating a frictional fit there around.

Figure 13:
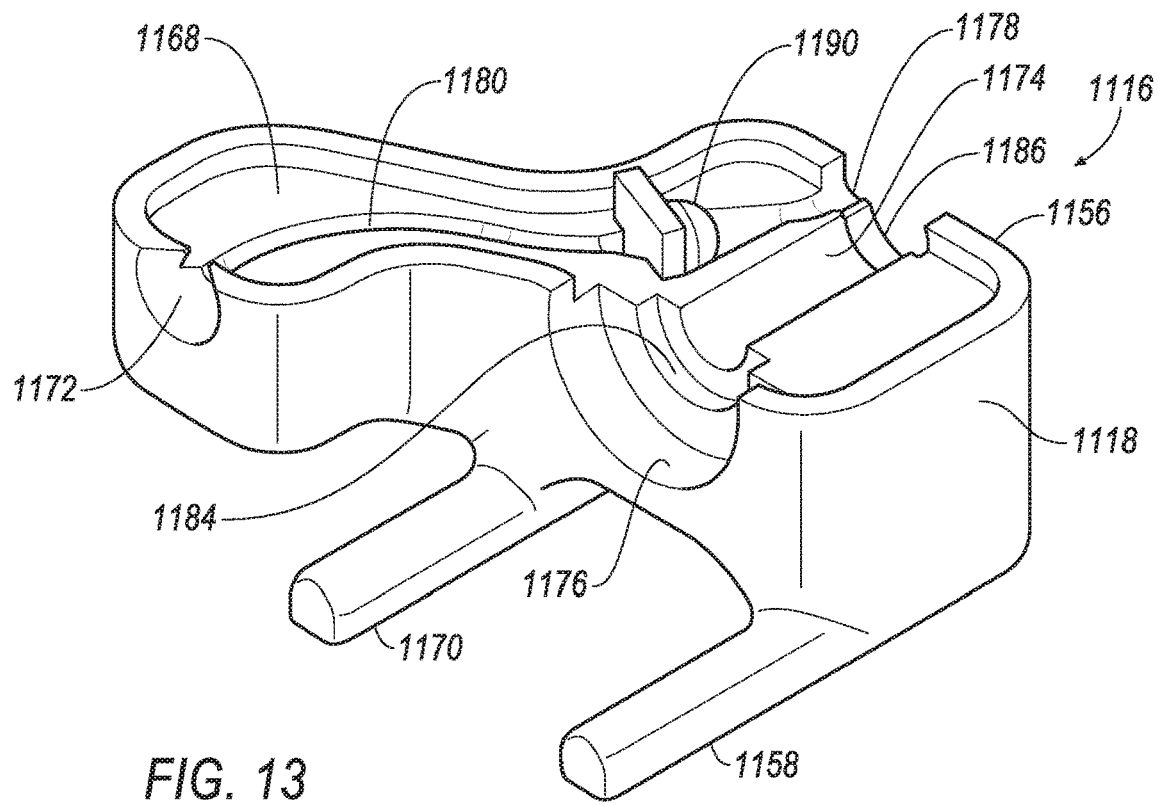
FIG. 13 is perspective, cross-sectional view of the attachment hub of FIG. 11.

Referring now to FIG. 13, a perspective cross-sectional view of the attachment hub 1116 is shown. The attachment hub 1116 may include a third projection 1170. The third projection 1170 may mimic the shape of the first projection 1158, as described above. The hub body 1118 may define a sleeve channel 1174 extending from the distal end 1156 through to a proximal end 1176 of the attachment hub 1116 and may form openings at each respective and 1156, 1176. These openings may be referred to herein as a first sleeve opening 1184 and the second sleeve opening 1186. The sleeve channel 1174 may be configured to retain at least a portion of the sleeve 1110 with in the hub body 1118.

The attachment hub 1116 may also include a wire channel 1180. The wire channel may extend from the channel opening 1172, also referred to as the first channel opening 1172, within the wire housing portion 1168 to the hub body and define a second channel opening 1178 at the distal end 1156 of the attachment hub 1116. The second channel opening 1178 may be arranged adjacent to the second sleeve opening 1186.

Figure 14:
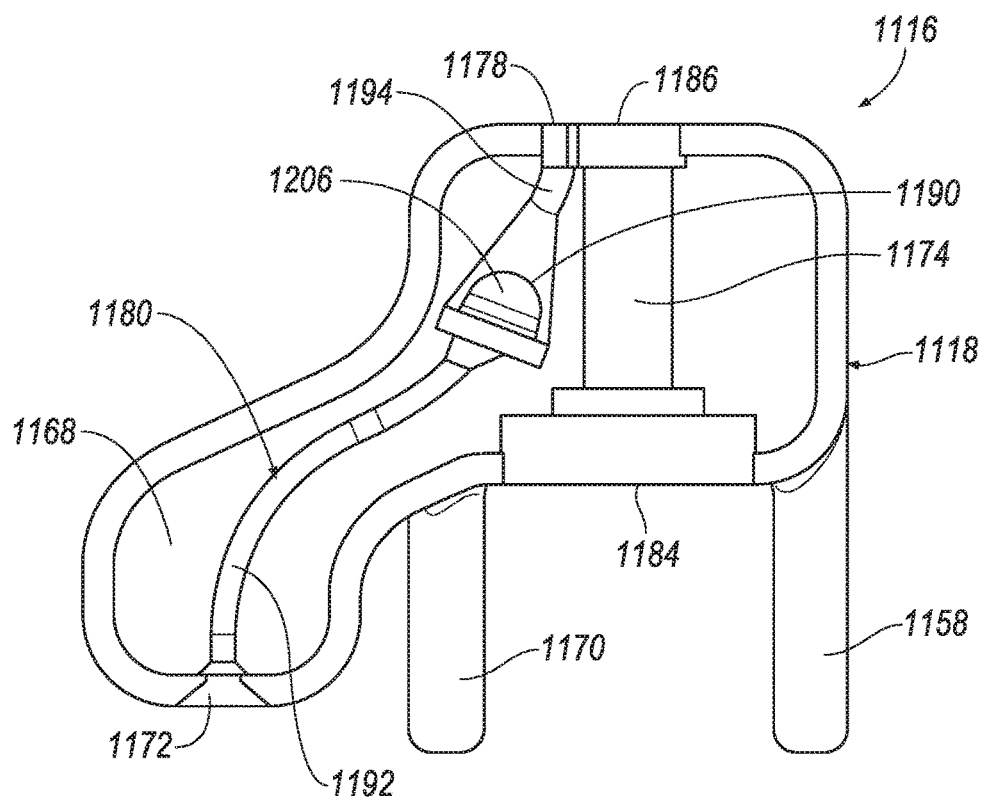
FIG. 14 is cross-sectional view of the attachment hub of FIG. 13.

The wire channel 1180 may be configured to maintain at least one wire or cable within the channel 1180. A light device 1190 may be arranged along the wire channel 1180. The light device 1190 may include a light source configured to supply or illuminate at least a portion of the optic channel 1108 (as shown in FIG. 11). Referring now to FIG. 14, the wire channel 1180 may include a first channel 1192 and a second channel 1194. The first channel 1192 may be arranged between the first channel opening 1172 and the light device 1190 and may be configured to provide a wire (e.g., cord 426) from the power source to the light device 1190. The second channel 1194 may be defined between the light device 1190 and the second channel opening 1178 and may be configured to maintain a fiber optic cable, configured to deliver illumination to the distal end of the sleeve 1110.

The LEDs may provide targeted illumination to a specific surgical site via the fiber optic device 1112 without otherwise causing a distraction or affecting other external room lighting. Although not illustrated in FIG. 14, the fiber optic device or devices 1112 may be retained within the fiber optic channel 1108. The channel 1108 may be arranged within the second channel opening 1178. The fiber optic channel 1108 may be arranged so that the fiber optic devices 1112 abut or nearly abut the light source 1206.

Figure 15:
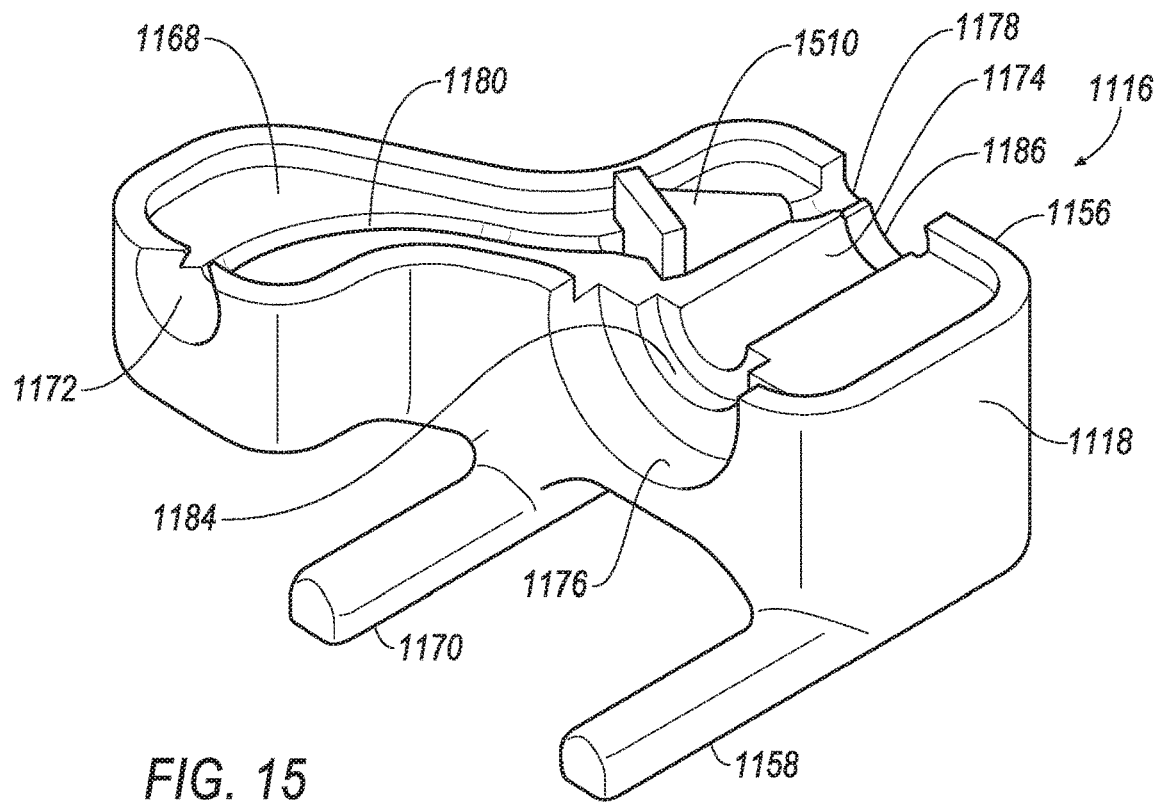
FIG. 15 is perspective, cross-sectional view of another embodiment of the attachment hub of FIG. 11.
Figure 16:
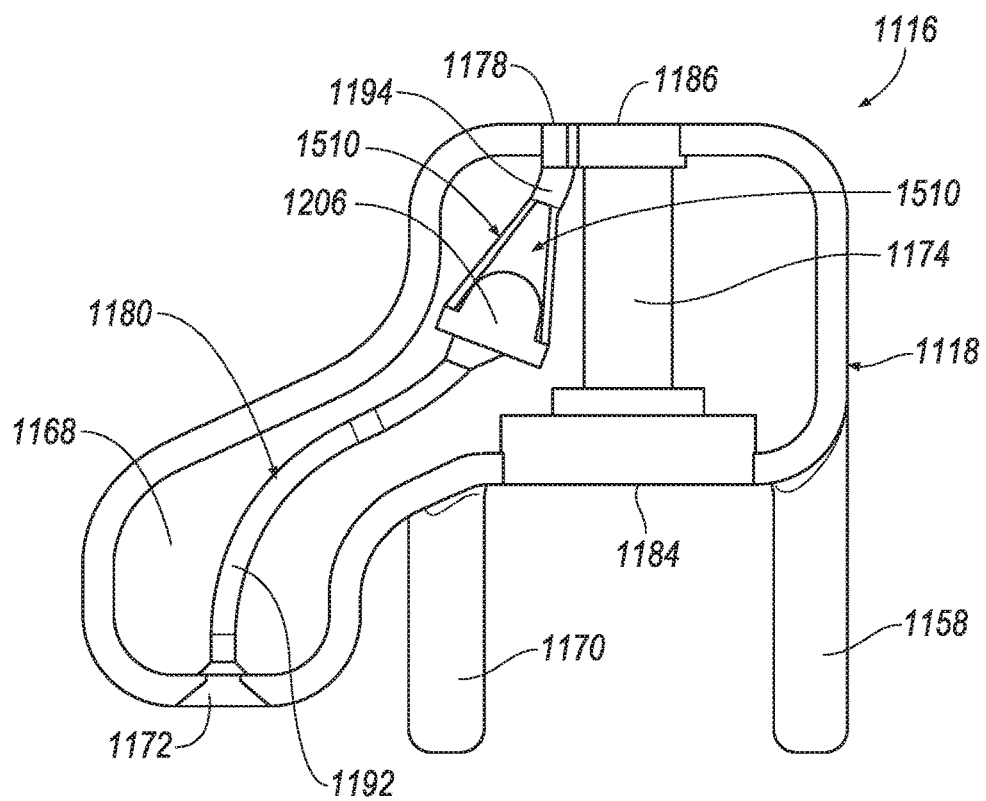
FIG. 16 is a plane view of the attachment hub of FIG. 15.

FIG. 15 illustrates a perspective cross-sectional view of another example attachment hub 116. The attachment hub 1116 may include a light directing device 1510 configured to surround at least a portion of the light source 1206 (as shown in FIG. 16). The light directing device 1510 may be a reflector or lens configured to reflect and focus light towards the attachment portion 1512. The light directing device 1510 may include a conical metal piece configured to surround the light source 1206 and configured to reflect the light created by the light source 1206 to an attachment portion 1512. The attachment portion 1512 may be the location within the second channel 1194 where in and of the fiber optic device 1112 is seated. That is, all of the light from the light source 1206 may be focused to the end of the fiber optic device 1112.

FIG. 17A and FIG. 18 illustrate perspective views of a portion of the illumination device of FIG. 11. FIG. 17B is a cross-sectional view of the sleeve 1110 and the channel 1108 of FIG. 17B. The sleeve 1110 and the fiber optic channel 1108 may be received at the distal end of the attachment hub 1116. The second projection 1160 and the wire housing portion 1168 grasp the rim 1154 to maintain the illumination device 1102 in an installed state/condition. To remove the illumination device 1102, a user may pull the second projection 1160 away from the rim 1154 at the tapered end 1166, thus releasing the force exerted thereby and permitting the wire housing portion 1168 to be slid away from the lip 1162.

Further, during assembly, the first portion 1202 may receive power supply wires, fiber optic cable, light sources (e.g., LEDs), within the wire channel 1180 (as shown in FIG. 13). Once these components have been appropriately placed, the second portion 1204 may be snapped onto the first portion 1202. At the surgical site, the hub 1116 may then be snap-fit onto the rim 1154. In another example, the two portions 1202, 1204 may be snapped together to encompass a portion of the upper housing 1152. That is, a bottom portion (e.g., first portion 1202) may be placed at the bottom of the upper housing 1152 around the lip followed by a top portion (e.g., second portion 1204) being placed at the top of the upper housing 1152 and snapped onto the bottom portion.

The sleeve 1110 and fiber optic channel 1108 may also be placed into their respective channels prior to assembly of the two portions. In one example, the sleeve 1110 may be inserted over the outer cannula 44 at the distal end thereof. The first portion 1202 may then be placed under the rim 1154 of the upper housing 1152 whereby the sleeve 1110 and fiber optic channel 1108 are received by the second sleeve opening 1186 and the second channel opening 1178, respectively. The second portion 1204 may then be placed on top of the rim 1154 and snapped onto the first portion 1202.

Figure 19:
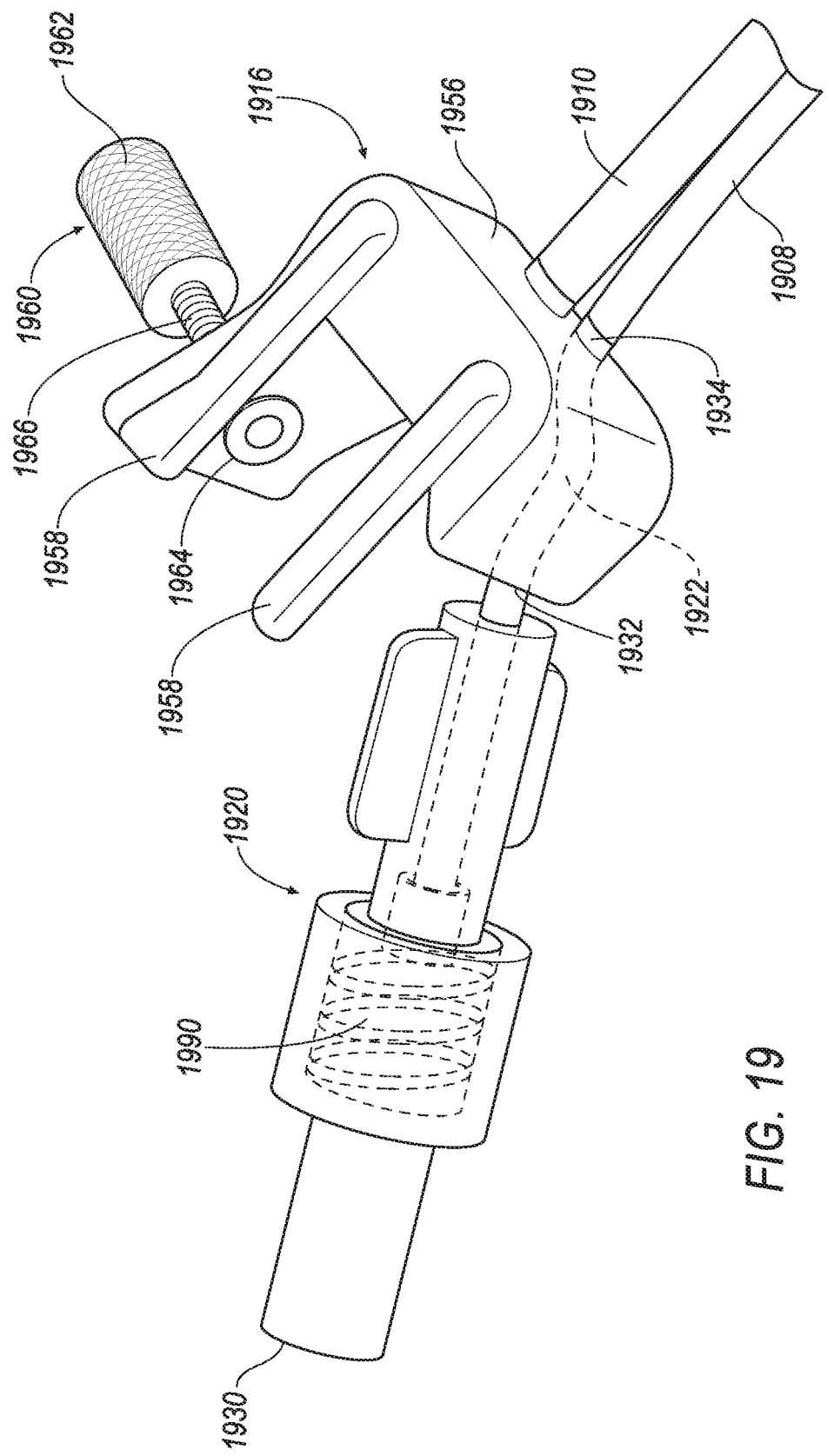
FIG. 19 is a perspective view of another illumination device.

FIG. 19 illustrates another example attachment hub 1916 having at least one first projection 1958, or a plurality of first projections 1958, as shown in FIG. 19. The hub 1916 may include a cable feed device 1920. The cable feed device 1920 may have a hollow cylinder-like shape configured to accept a fiber optic cable, or other cables, and to aid in inserting the cable into an optic channel 1908 arranged on the sleeve 1910. The cable feed device 1920 may have a distal end 1930 and a proximal end 1932.

The hub 1916 may define an interior channel 1922 configured to receive cable from the proximal end 1932 of the feed device 1920. The channel 1922 may extend from the proximal end 1932 of the feed device 1920 to a proximal end 1934 of the optic channel 1908 at the distal end 1956 of the hub, thus facilitating feeding of the cable into the optic channel 1908.

The hub 1916 may include an attachment mechanism 1960 configured to attach the hub 1916 to the handpiece 42. The attachment mechanism 1960 may include at least one pin 1962 at the second projection 1958. The pin 1962 may include screw-like helical ridge 1966. The second projection 1958 may define a ridged hole 1964 configured to receive and engage the pin 1962. The pin 1962 may be selectively screwed and unscrewed within the hole 1964. Upon screwing the pin 1962 through the hole 1964, the pin 1962 may abut the rim (as shown in FIG. 11) and frictionally engage the rim 1154 to aid in maintaining the hub 1916 to the handpiece 42 at the rim 1154 by applying force via the pin 1962.

Although shown as a screw-like device, the pin 1962 may also be a spring pin when in its resting state, apply force against the rim 1154. The pin 1962 may be pulled back against the tension of the spring (not shown) to release the force applied to the rim 1154.

Figure 20:
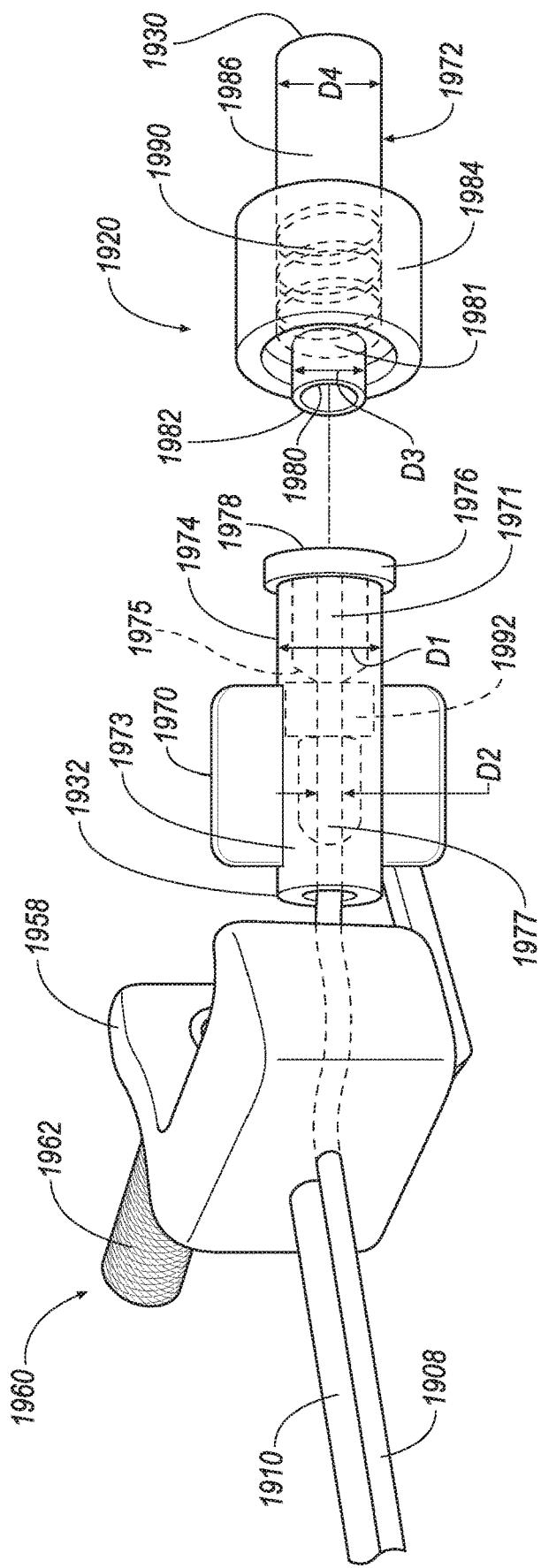
FIG. 20 is a perspective view of the illumination device of FIG. 19.

FIG. 20 illustrates another view of the hub 1916 of FIG. 19 whereby the feed device 1920 is shown in a disassembled state. The feed device 1920 may include a first part 1970 and a second part 1972. The first part 1970 may be proximal to the hub 1916 and configured to be engaged with the interior channel 1922. The first part 1970 may include a body portion 1973 and a first projection 1974 extending from the body portion 1973. The first projection 1974 may include a lip 1976 at a first end 1978. The first projection 1974 may define a hollow first projection channel 1971 defining a first diameter $D_1$. The body portion 1973 may include a tapered channel 1975 wherein the tapered channel 1975 opens to the first projection channel 1971 and tapers to a body channel 1977. The body channel 1977 may define a second diameter $D_2$ being less than the first diameter $D_1$ of the first projection channel 1971.

The second part 1972 may include a second projection 1980 at a second end 1982 whereby the second projection 1980 may be configured to be received by the first projection 1974 of the first part 1970. The second projection 1980 may define a second projection channel 1981 having a third diameter $D_3$. The third diameter $D_3$ may be less than the first diameter $D_1$ such that the second projection 1980 may be configured to be received by the first projection 1974 of the first part 1970 in the installed state. The second part 1972 may further include an outer cap 1984 configured to circumferentially surround the first projection 1974 in the installed state, as shown in FIG. 19. The distal end 1930 of the feed device 1920 may define a fourth diameter $D_4$. The fourth diameter $D_4$ may be larger than the third diameter $D_3$ creating a tapered cone-like second channel 1986 inside of the second part 1972. The cone-like channel 1986 may aid in guiding the wires into and through the feed device 1920.

In an installed state, the lip 1978 of the first part 1970 may be received by the cap 1984 of the second part 1972 and may form a lock-fit between the cap 1984 and the second projection 1980. The lock-fit may be created by snapping or screwing the lip 1976 into the cap 1984. As shown by way of example in FIGS. 19 and 20, the cap 1984 may include a helical ridge within it. The lip 1976 may be configured to be screwed into the cap 1984 via the helical ridge 1990.

A valve 1992 may be included within the first projection channel 1971. The valve 1992 may be a cylindrical silicone ring configured to be flexible in both the axial and radial directions. The valve 1992 may be configured to secure the fiber optic cable within the channels of the feed device 1920. Upon a screwing of the cap 1984, the second projection 1980 may be pushed into the first projection channel 1971. The second projection 1980 may abut the valve and apply pressure to the valve 1992 as the cap 1984 is screwed. In response to the axial depression caused by the second projection 1980, the valve 1992 may in turn extend radially inwardly to compensate for the axial depression. The valve 1992 may create a pinching effect on the cable within the first projection channel 1971 to maintain the cable within the channel and prevent movement thereof. Thus, as the first part 1970 and the second part 1972 are screwed together, the valve 1992 creates a secured hold on the outer diameter of the cable. In one example, a Tuohy Borst™ fitting may be used for the feed device 1920.

Additionally or alternatively, a Tuohy Borst™ fitting may be fixed to the body portion 1973 of the first part 1970 and the second part 1972 may be eliminated from the design. In this implementation, the valve 1992 may also be eliminated. Furthermore, in another implementation, first projection 1974 may be eliminated. The Tuohy Borst™ fitting may thus be configured to maintain the fiber optic cable at a fixed, but adjustable, location.

The cable, or cables, may be inserted at the distal end 1930 of the second part 1972 of the feed device 1920. The cable may be fed through the second channel 1986, then subsequently through the first projection channel 1971 and into the body channel 1977. The diameter of the channels may progressively decrease from the distal end 1930 to the proximal end 1932 of the feed device 1920 in an effort to feed the cable into the interior channel 1922 and subsequently the optic channel 1908. Thus, the cable may be easily inserted at a wider channel at the distal end 1930 and pushed through to the smaller optic channel 1908 without realizing any obstructions and without buckling within the channels.

Accordingly, a low-profile illumination device is disclosed herein for supply light to a surgical site. The add-on device may be used independently or in addition to other external light sources, to decrease the effects of shadowing, or provide light to areas absent of the desired light at the surgical site. Moreover, a targeted light may be supplied based on specific surgical requirements and may be customizable for various procedure types.

FIG. 21 illustrates another example tissue cutting device 2140 including a handpiece 2142. FIG. 21 also illustrates another example illumination device 2102 that may be arranged around the outer cannula 44 (not shown in FIG. 21) and configured to supply light to a surgical site via one or more optical fibers to form a fiber optic cable arranged on a sleeve 2110. The sleeve 2110 may form a tube-like channel configured to surround the outer cannula 44. The fiber optic device 1112 may include a fiber optic channel 2108 configured to retain at least one fiber optic cable (not shown) configured to supply light to the surgical site at the distal end of the outer cannula 44. The fiber optic cable may extend from within the hub 2116 through the end of the channel 2108, delivering light to the surgical site. The sleeve 2110 and the channel 2108 may be connected via molding, soldering, heat shrinking, etc. In one example, the fiber optic channel 2108 may be the fiber optic cable. That is, a separate channel may not be necessary and instead the fiber optic cable may be directly adhered to the sleeve 2110.

An attachment hub 2116 may be configured to attach and detach from the outer cannula 44 at the upper housing 2152 of the handpiece 2142. The attachment hub 2116, similar to the description set forth above for the attachment hub 1116 of FIG. 11, may be configured to "snap" on to a portion of the upper housing 2152.

Figure 22A:
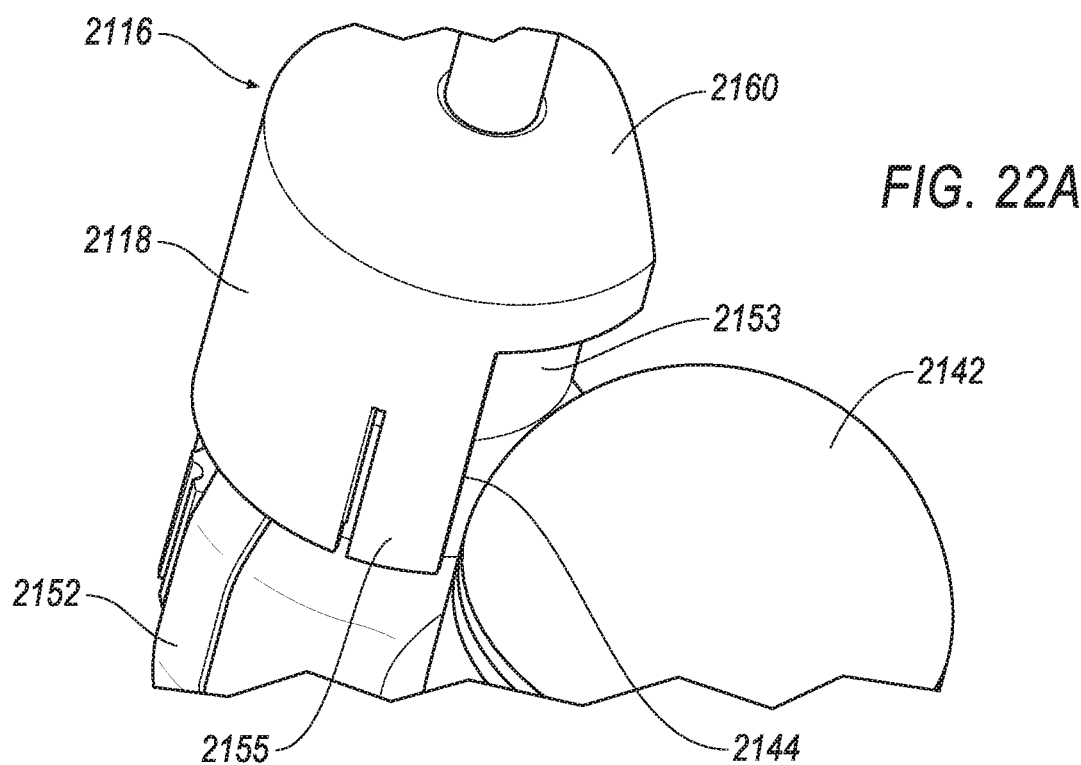
FIGS. 22A and 22B are perspective views of a portion of the hub of FIG. 21.
Figure 22B:
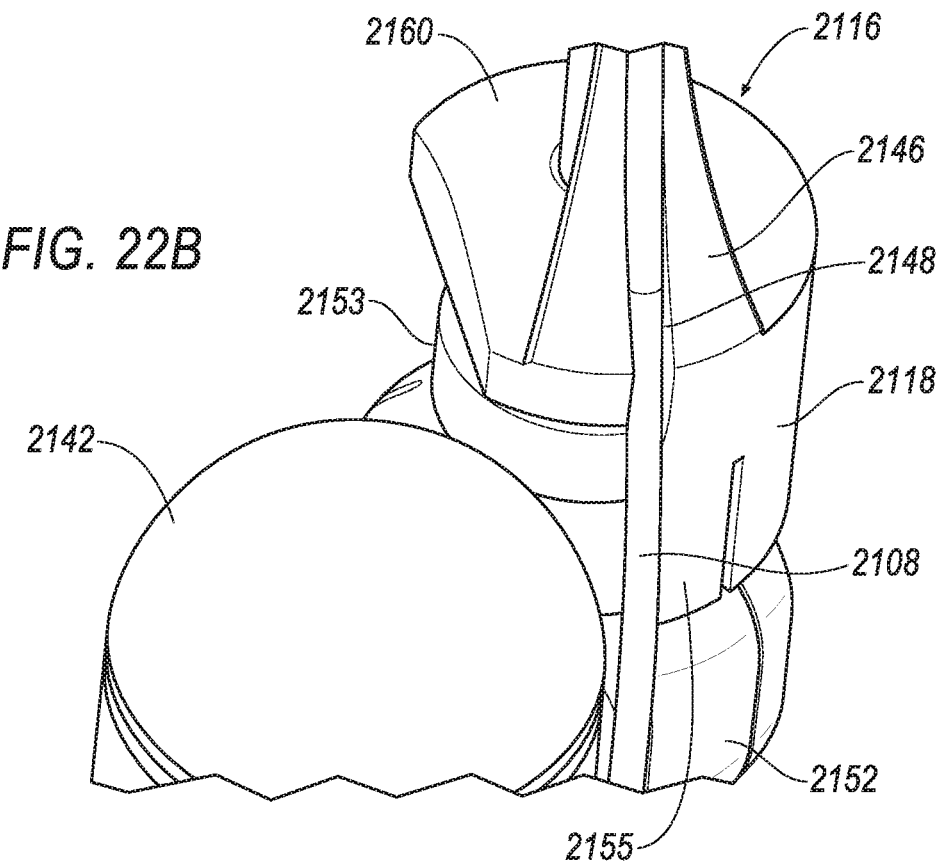

Referring to FIGS. 22A and 22B, the attachment hub 2116 may include a cylindrical or semi-cylindrical body 2118 configured to selectively attach to the upper housing 2152. In the examples discussed herein, the body 2118 may be configured to connect to the upper housing 2152 about a distal end 2153 at a distal end of the upper housing 2152. The hub 2116 may form an end cap 2160 configured to cover the distal end of the upper housing 2152 when the hub 2116 is in an installed position. The cylindrical body 2118 may extend from the cap 2160 and cover at least a portion of the distal end 2153. The body 2118 may extend around approximately 50% of the distal end 2153, leaving a portion of the distal end 2153 exposed.

The hub 2116 may be rotatable about the distal end 2153. In one example, the hub 2116 may define a track (not shown) on the inner surface of the hub 2116. The track may be configured to receive the distal end 2153 where the track may be movable about the rim permitting the hub 2116 to be rotatable about the upper housing 2152.

As shown in FIGS. 22A and 22B, the cylindrical body 2118 may extend around a portion of the distal end 2153, leaving an exposed portion. The exposed portion may allow the hub 2116 to rotate about the upper housing 2152 without the hub 2116 abutting the handpiece 2142. An edge 2144 of each end the cylindrical body 2118 may abut the handpiece 2142, preventing the hub 2116 from rotating further. Thus, the hub 2116 may rotate between a first position where a first edge (e.g., edge 2144 of FIG. 22A) abuts the handpiece 2142 and a second position where a second edge (e.g., the ends opposite that of edge 2144) abut the handpiece 2142. The hub 2116 may have a certain degree of rotation permitted by the exposed portion. The larger the exposed portion and the smaller the cylindrical body 2118, the larger the degree of rotation of the hub 2116. In one example, the hub 2116 may have 120 degrees of rotation. More or less rotation may also be permitted.

In addition to the hub 2116 being rotatable, the hub 2116 may also be arranged at a fixed location with respect to the upper housing 2152. Further detail on the attachment of the hub 2116 to the upper housing 2152 is described herein with respect to FIGS. 26-28 below.

The hub 2116 may include a guide portion 2146 arranged at the cap 2160. The guide portion 2146 may define a guide track 2148 configured to receive and maintain the fiber optic channel 2108. The channel 2108 may extend from the guide track 2148 along the sleeve 2110. In the example where the hub 2116 is rotatable with respect to the upper housing 2152, the guide track 2148 may maintain the channel 2108 therein during such rotation of the hub 2116.

Referring to FIG. 21, the tissue cutting device 2140 also includes an optic attachment assembly 2230 that provides the fiber optic cable or wire (not shown) to the channel 2108. The optic attachment assembly 2230 may include a housing 2232 configured to house a light source (not shown) such as LEDs.

Referring back to FIG. 23, the housing 2232 may include the light source(s) (not shown). The housing 2232 may also include a heat sink 2240 and a cage 2242 surrounding the same. The heat sink 2240 may be configured to absorb heat created by the light sources such that heat is not delivered to the distal end of the tissue cutting device 2140. The light sources may provide light to the surgical site. The light sources may be similar to light sources 406, including light emitting diodes (LEDs) or other low-energy consuming light sources 406. The light sources may also be similar to the light device 1190 of FIG. 11 and may include a light source configured to supply or illuminate at least a portion of the fiber optic channel 2108.

The heat sink 2240 may be made out thermally conductive material, including but not limited to copper, aluminum, graphite foam, diamond, composite materials such as copper-tungsten pseudoalloy, silicon carbide, dymalloy, berllium beryllium oxide, etc., or any combination hereof. The heat sink 2240 may be configured to allow heat to dissipate from the light source, thus preventing degradation or failure of the light source emission by thermal destruction. The cage 2242 may arranged about the heat sink 2240 and may define one or more openings 2246. The openings 2246 may expose portions of the heat sink 2240 to increase air exposure thereto, thus further facilitating cooling. The cage 2242 may be formed of a non-heat conductive material and may prevent a user from coming into contact with heat produced by the light source, as well as other components such as power sources, etc.

The cage 2242 may include a clamp 2248 configured to attach the cage 2242 to the handpiece 2142 at the sleeve 2110. The clamp 2248 may also connect to other portions of the handpiece 2142 including other channels, cannulas, lines, etc. The clamp 2248 may be configured to selectively connect around the sleeve 2110 and a vacuum line 2212 or other line or cannula in an installed position. The clamp 2248, including the cage 2242, may be made of a pliable but rigid material, allowing the clamp 2248 to be expanded in order to disengage with the sleeve 2110 and to be biased inward to clamp onto the sleeve 2110 in the installed position.

The optic attachment assembly 2230 may include a connector 2260 configured to connect to a cable feed device 2220 arranged on the handpiece 2142. The connector 2260 may be connected to the housing 2232, or cage 2242 and/or the heat sink 2240. The connector 2260 may be a Luer Lock mechanism. In one example, the cable feed device 2220 may be similar to the cable feed device 1920 shown and described with respect to FIGS. 19 and 20. In another example, the cable feed device 2220 of FIG. 23 may be similar to the first part 1970 of FIG. 20, where the cable feed device 2220 includes a tapered channel. The connector 2260 and cable feed device 2220 may aid in stabilizing the wire or cable so that the wire may be inserted into the optic channel 2108. The housing 2232 may receive a wire 2266 configured provide power to the light sources.

Figure 23:
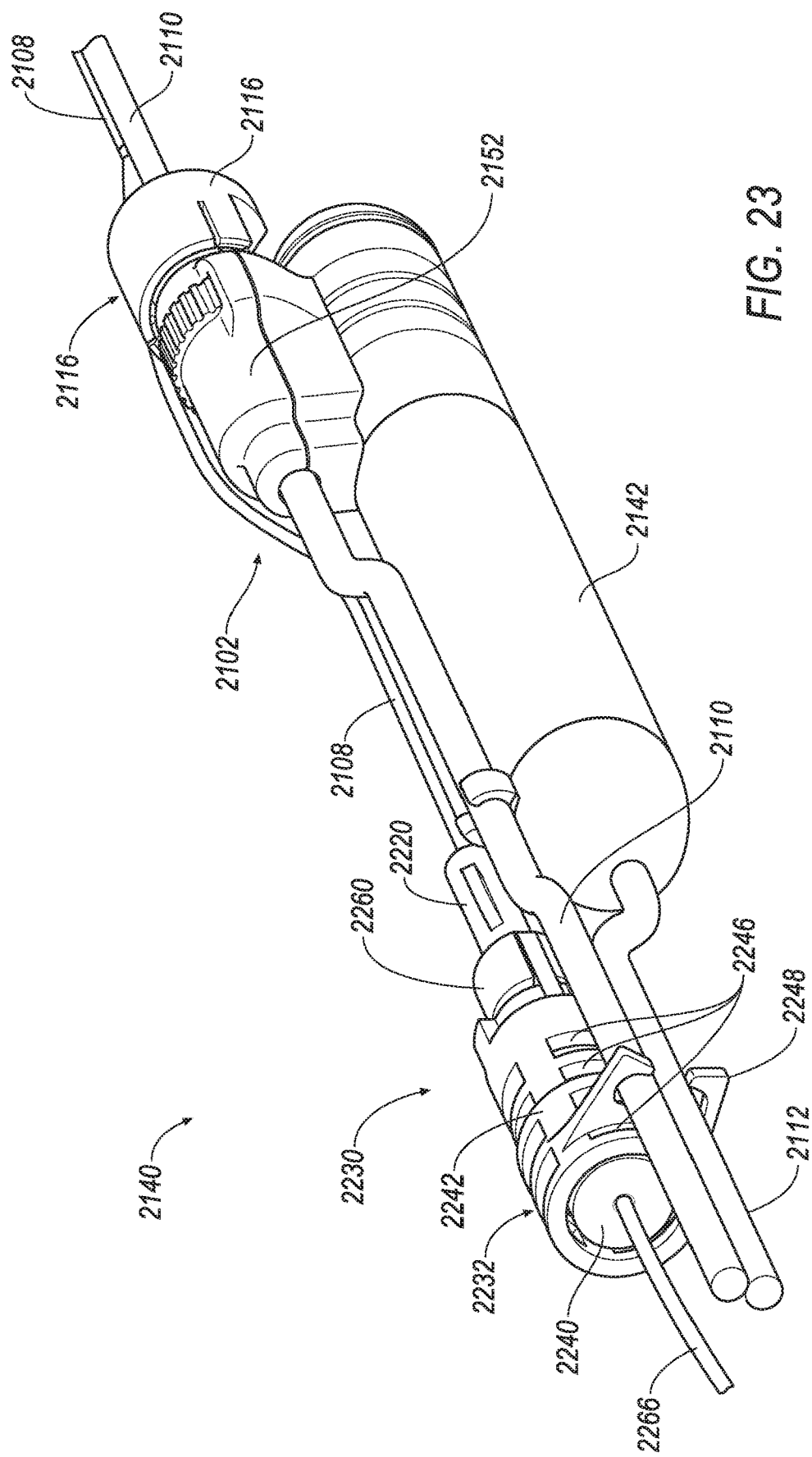
FIG. 23 is a perspective view of the tissue cutting device of FIG. 21.
Figure 24:
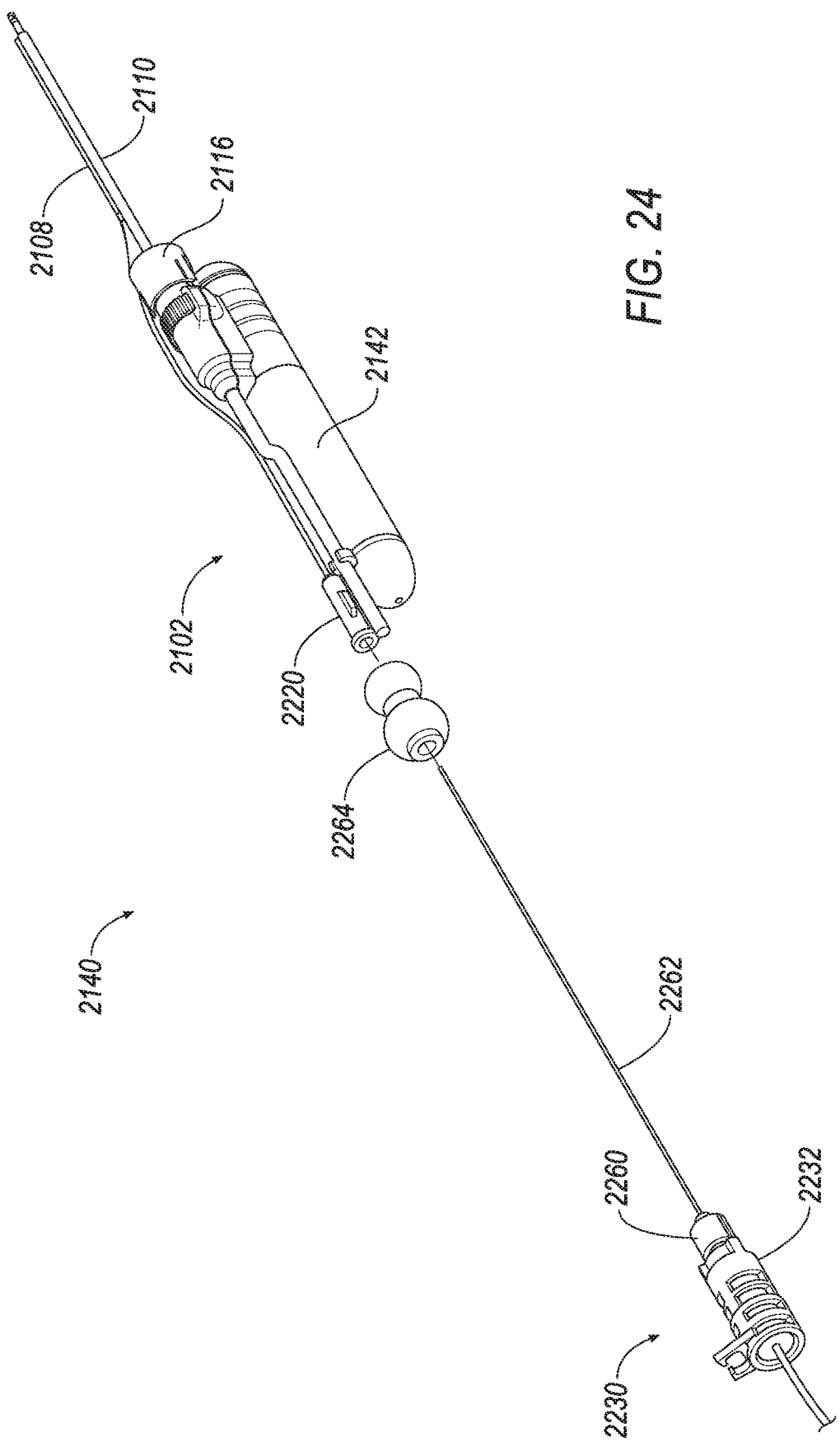
FIG. 24 is an exploded view of the optic attachment assembly of FIG. 23.

FIG. 24 illustrates an exploded view of the optic attachment assembly 2230 and the handpiece 2142. The attachment assembly 2230 may include a wire 2262 (or fiber optic cable 2262). Prior to attachment to the handpiece 2142, the cable feed device 2220 may receive the wire 2262 of the attachment assembly 2230. The cable feed device 2220 may receive and guide the wire via the tapered channel (not shown in FIG. 24) into the channel 2108. In an installed position, as shown in FIG. 23, once the wire 2262 is fully inserted into the channel 2108, the connector 2260 may connect to the cable feed device 2220.

In another example, as shown in FIG. 24, an adaptor 2264 may be arranged between the attachment assembly 2230 and the cable feed device 2220. The adaptor 2264 may be a Tuohy Borst™ fitting. In this example, the cable feed device 2220 may be similar to the first part 1970 of FIGS. 19 and 20, and the second part 1972 may be eliminated from the design. In this implementation, the Tuohy Borst™ fitting may be configured to maintain a fiber optical cable at a fixed, but adjustable location. The adaptor 2264 may be implemented in an example where an external light and or laser source is being used.

Figure 25:
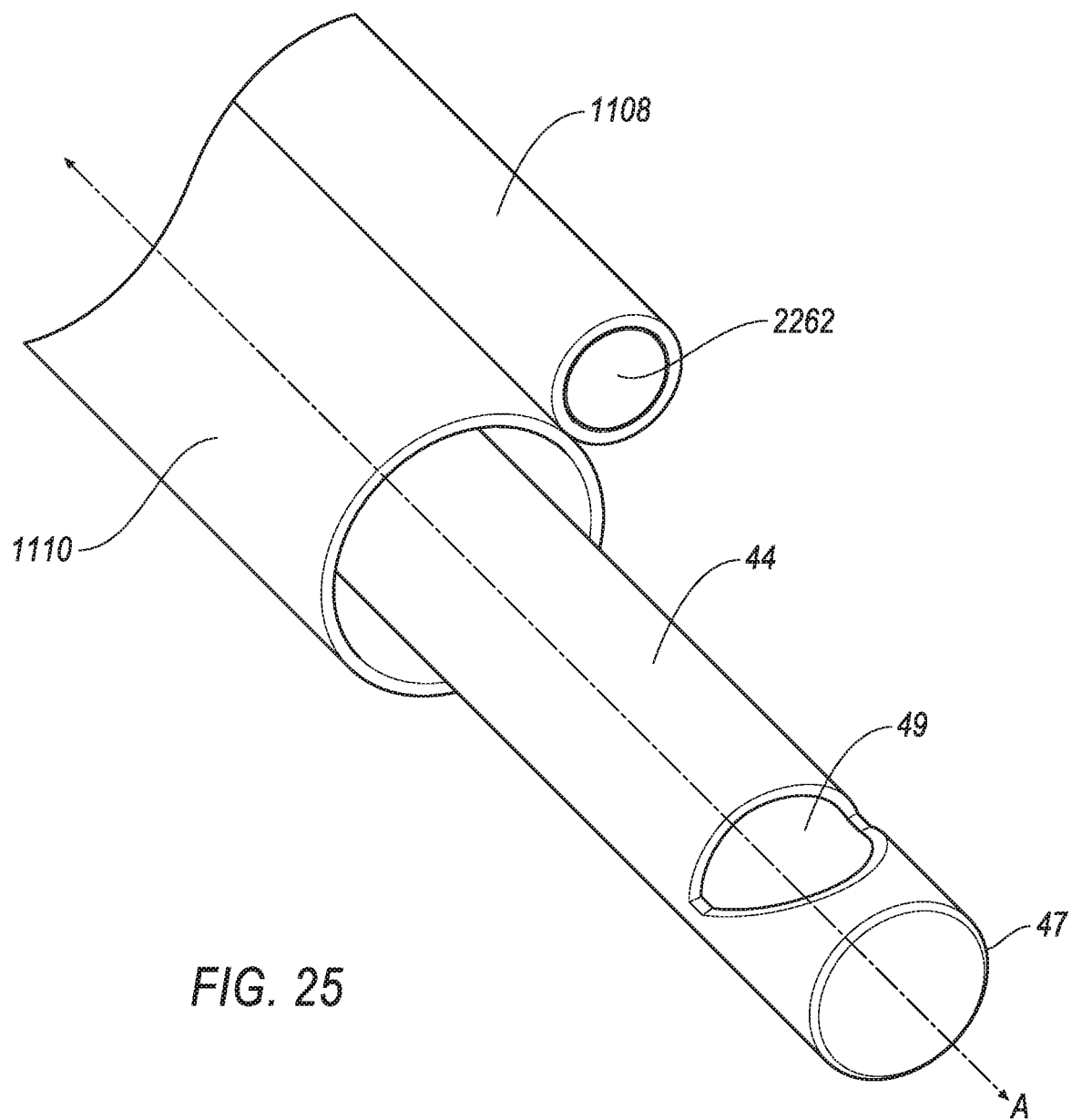
FIG. 25 is a perspective view of a portion of the illumination device of FIG. 11.

FIG. 25 illustrates a perspective view of a portion of the illumination device of FIG. 11. As explained above with respect to FIG. 11, the sleeve 1110 may form a tube-like channel configured to surround the outer cannula 44. The sleeve 1110 may extend along an axis A. As best explained and illustrates with respect to FIGS. 2 and 3, the outer cannula 44 may include an open proximal end 45, a closed distal end 47, and a distal opening 49 proximate distal end 47. An inner cannula 76 may be partially disposed in an outer cannula lumen (not visible in FIG. 25). Inner cannula 76 is configured to reciprocate within outer cannula lumen and to cut tissue samples entering outer cannula 44 via outer cannula distal opening 49, The fiber optic device 1112 may include a fiber optic channel 1108 configured to retain at least one fiber optic cable 2262 or wire configured to supply light to the surgical site at the distal end of the outer cannula 44. The fiber optic channel 1108 may be arranged off-set from the axis A while the distal end of the fiber optic channel is arranged proximate to the distal end of the sleeve 1108. The fiber optic cable 2262 may extend to the end of the channel 1108, delivering light to the surgical site. The sleeve 1110 and the channel 1108 may be connected via molding, soldering, heat shrinking, etc. While the example in FIG. 25 illustrates that the fiber optic cable 2262 is flush with the distal end of the channel 1108, the cable 2262 may protrude or retract relative to the channel 1108. That is, the cable 2262 may extend beyond the sleeve 1110, or may be recessed therein.

Figure 26:
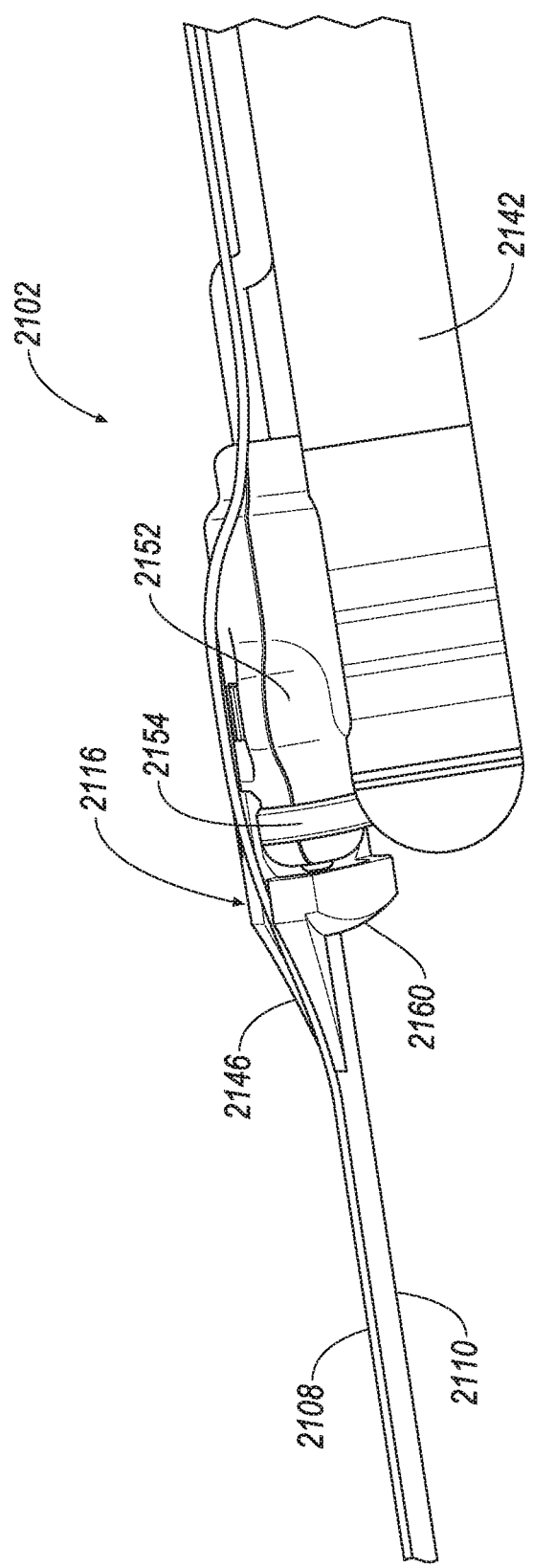
FIG. 26 is a perspective view of a portion of the illumination device of FIG. 21.
Figure 27:
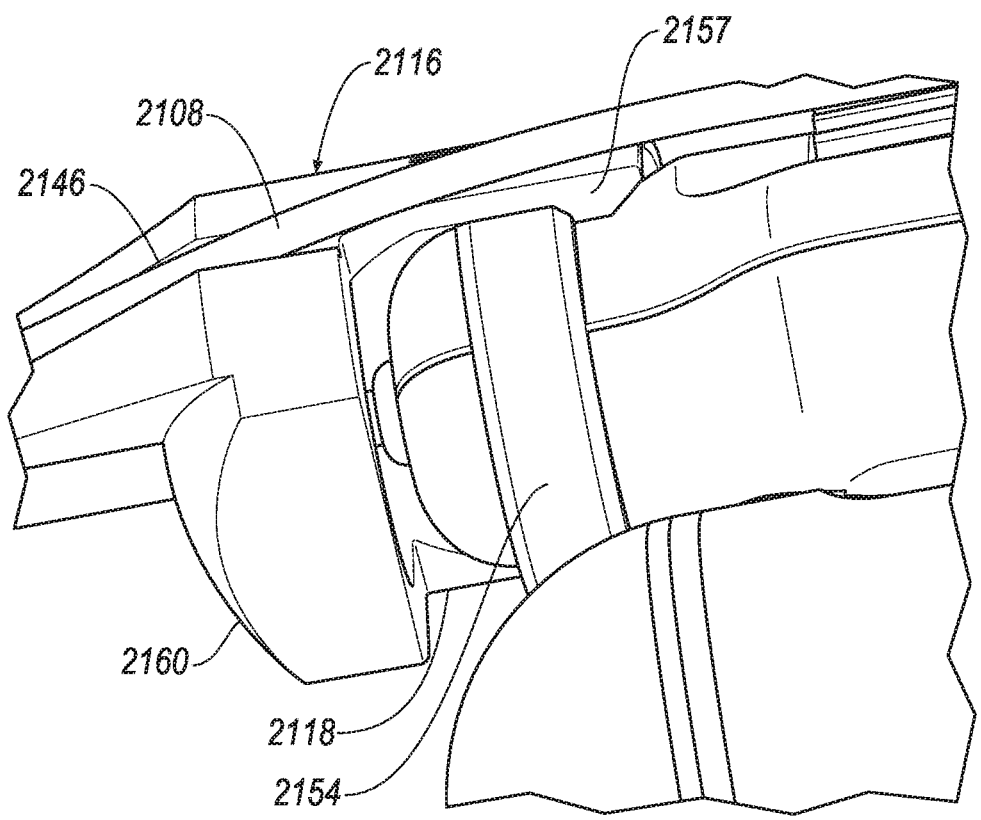
FIG. 27 is a perspective view of the attachment hub of FIG. 21.
Figure 28:
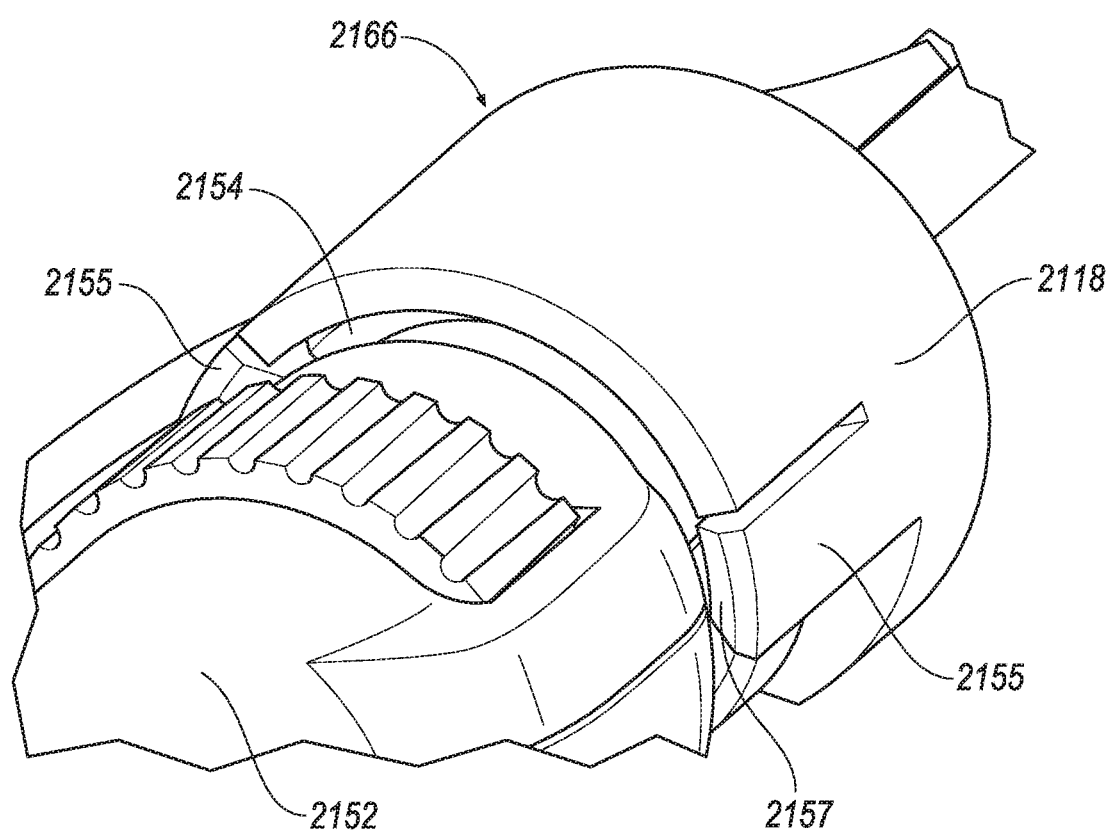
FIG. 28 is another perspective view of the attachment hub of FIG. 21.

FIGS. 26-28 illustrate perspective views of a portion of the illumination device of FIG. 21. The attachment hub 2116 may be selectively attached to the upper housing 2152. The upper housing 2152 may include a ring 2154 arranged at the distal end 2153 of the upper housing 2152. The ring 2154 may extend circumferentially around the distal end 2153 of the upper housing 2152.

The hub 2116 may include at least one snap feature 2155 configured to engage the ring 2154 and maintain the hub 2116 on the upper housing 2152. The snap feature 2155 may be included and defined by the semi-cylindrical body 2118. In the example shown in the figures, the semi-cylindrical body 2118 may define two snap features 2155 at each end of the cylindrical body 2118. The snap features 2155 may be spaced from one another about the cylindrical body 2118.

The snap feature 2155 may include a tapered end 2157 defining a concave-like shape configured to engage the ring 2154 to secure the attachment hub 2116 to the upper housing 2152. The snap feature 2155 may be pliable with respect to the cap 2160 in that the snap feature 2155 may deflect outwardly over the ring 2154 and then retract inwardly once the ring 2154 has been cleared so that the tapered end 2157 may engage the underside of the ring 2154 to secure the attachment hub 2116 to the upper housing 2152.

While the snap feature 2155 may fix the attachment hub 2116 to the upper housing 2152 in a lateral direction, the hub 2116 may be radially movable with respect to the upper housing. That is, the hub 2116 may rotate with respect to the upper housing 2152, as explained above with respect to FIG. 22. Thus, the hub 2116 may selectively attach and detach from the upper housing 2152. In the installed state, the hub 2116 may rotate about the ring 2154, but otherwise be laterally fixed to the upper housing 2152.

It will be appreciated that the tissue cutting devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

While exemplary embodiments are described above, it is not intended that these embodiments describe all possible forms of the invention. Rather, the words used in the specification are words of description rather than limitation, and it is understood that various changes may be made without departing from the spirit and scope of the invention.

Additionally, the features of various implementing embodiments may be combined to form further embodiments of the invention.

What is claimed:

1. A tissue removal system, comprising:
a tissue removal device including a handpiece and an upper housing, and configured with an outer cannula and an inner cannula disposed in the outer cannula,
an illumination device including a hub configured to selectively attach to the tissue removal device at the upper housing and having a sleeve arranged at least partially on the outer cannula, the hub defined by a semi-cylindrical body that partially surrounds a distal end of the upper housing, the semi-cylindrical body having a cut-out portion that is defined between first and second edges,
a snap feature formed within the semi-cylindrical body,
an optic channel defining an opening and arranged offset from the sleeve, and
a light source arranged within the channel and configured to supply light from the opening to a surgical site.

2. The system of claim 1, wherein the light source is a fiber optic cable.

3. The system of claim 2, wherein the fiber optic cable extends outwardly from the sleeve opening.

4. The system of claim 1, wherein the semi-cylindrical body is configured to cover a portion of the upper housing.

5. The system of claim 4, wherein the hub is rotatable with respect to the upper housing.

6. The system of claim 1, wherein the sleeve opening is proximal to a distal end of the outer cannula opening.

7. An illumination device for tissue removal system, comprising:
a sleeve arranged at least partially on an outer cannula of a tissue removal system, the sleeve including a light source to provide light to a surgical site at a distal sleeve opening;
a hub including a semi-cylindrical body configured to selectively attach around a distal end of an upper housing of the tissue removal system and maintain the sleeve therein, the semi-cylindrical body being rotatable with respect to the upper housing; and
wherein the semi-cylindrical body defines at least one snap feature configured to engage a portion of the upper housing, wherein the snap feature is defined by a slit formed in the semi-cylindrical body, the slit extending from a proximal end of the semi-cylindrical body toward a distal end of the semi-cylindrical body along a portion of a length of the cylindrical body.

8. The device of claim 7, wherein the semi-cylindrical body is rotatable between a first position where a first edge of the semi-cylindrical body abuts a handpiece and a second position where a second opposite edge of the semi-cylindrical body abuts the handpiece.

9. The device of claim 7, wherein the semi-cylindrical body is rotatable approximately 120 degrees.

10. The device of claim 7, wherein the snap feature engages the upper housing and is configured to fix the hub to the upper housing to prevent movement of the hub in a lateral direction with respect to the upper housing.

11. The device of claim 10, wherein the snap feature is configured to engage a ring arranged on the upper housing, wherein the hub is configured to rotate about the ring.

12. An optic attachment assembly for tissue removal system, comprising:
a hub defined by a semi-cylindrical body, wherein the hub defines at least one snap feature configured to engage a portion of a housing of a tissue removal system, wherein the snap feature is defined by a slit formed in the semi-cylindrical body, the slit extending from a proximal end of the semi-cylindrical body toward a distal end of the semi-cylindrical body along a portion of a length of the cylindrical body;
a sleeve connected to the huh, the sleeve being sized to at least partially be disposed about an outer cannula of a tissue removal system, the sleeve including a fiber optic cable; and
a housing including a light source configured to provide light to the fiber optic cable, the housing including a cage surrounding the light source to prevent exposure to the light source, but the cage further having a plurality of openings, wherein the cage includes at least one clamp to selectively attach the housing to the tissue removal system.

13. The assembly of claim 12, wherein the housing includes a heat sink arranged around the light source to dissipate heat generated by the light source.

14. The assembly of claim 13, wherein the cage surrounds the heat sink and the plurality of openings in the cage to provide air exposure to the heat sink.

15. A tissue removal system, comprising:
a tissue removal device having a housing and configured with an outer cannula,
an illumination device including hub configured to selectively attach to the tissue removal device and having a sleeve arranged at least partially on the outer cannula, the hub including a semi-cylindrical body that partially surrounds a distal end of the housing,
a snap feature formed within the semi-cylindrical body, wherein the snap feature is defined by a slit formed in the semi-cylindrical body, the slit extending from a proximal end of the semi-cylindrical body toward a distal end of the semi-cylindrical body along a portion of a length of the cylindrical body, wherein the snap feature is pliable with respect to the semi-cylindrical body,
an optic channel defining an opening and arranged offset from the sleeve, and
a light source arranged within the channel and configured to supply light from the opening to a surgical site.

16. The system of claim 15, wherein the semi-cylindrical body comprises a first edge and a second edge that define an exposed portion therebetween.

* * * * *